United States Patent [19]

Yamazoe

[11] Patent Number: 5,719,665
[45] Date of Patent: Feb. 17, 1998

[54] METHOD AND APPARATUS FOR DETERMINING THE CONTENT OF INSOLUBLES IN OILS

[75] Inventor: Seigo Yamazoe, Saitama, Japan

[73] Assignees: Cosmo Research Institute; Cosmo Oil Co., Ltd., both of Tokyo, Japan

[21] Appl. No.: 555,757

[22] Filed: Nov. 9, 1995

[30] Foreign Application Priority Data

Nov. 10, 1994 [JP] Japan ................................. 6-301352
Sep. 20, 1995 [JP] Japan ................................. 7-266245

[51] Int. Cl.$^6$ .......................... G01N 33/28; G01N 21/00; G01T 1/167
[52] U.S. Cl. ...................... 356/70; 356/73; 250/301
[58] Field of Search ..................... 356/243, 70, 73, 356/436; 250/301

[56] References Cited

U.S. PATENT DOCUMENTS

| | | | |
|---|---|---|---|
| 3,936,192 | 2/1976 | Skala | 356/343 |
| 4,843,247 | 6/1989 | Yamazoe et al. | 250/573 |
| 5,194,910 | 3/1993 | Kirkpatrick, Jr. et al. | 356/70 |
| 5,400,137 | 3/1995 | Winslow et al. | 356/73 |
| 5,489,977 | 2/1996 | Winslow et al. | 356/73 |

FOREIGN PATENT DOCUMENTS

| | | | |
|---|---|---|---|
| A20346609 | 12/1989 | European Pat. Off. | |
| 2-49141 | 2/1990 | Japan | G01N 21/27 |

OTHER PUBLICATIONS

Vanous, R.D., "Turbidimetric Measurement of Strongly Colored Liquids Using a Ratio Turbidimeter," ISA Transactions, vol. 20, No. 3, 1981, Research Triangle Park, NC, US, pp. 91–95.

Bouquet, et al., "Mesure de la Teneur en Asphaltenes des Coupes Lourdes du Petrole par Spectrophotometrie," International Symposium on Characterization of Heavy Crude Oils and Petroleum Rsidues, Jun. 24 1984, Lyon, FR, pp. 196–199, XP 000121045.

Hangartner, et al., "New Maintenance Free Photometer for Measuring Sludge Concentration or Effluent Turbidity," Advances in Instrumentation, vol. 36, No. 2, Oct. 1981, Research Triangle Park, NC, US, pp. 165–173.

Mirsayapova, et al., "Rapid Method of Determination of Asphaltene Content in Petroleum Crudes and Products," Chemistry and Technology of Fuels and Oils, vol. 12, No. 9/10, NY, US, pp. 805–807, XP 00012050.

*Primary Examiner*—Frank G. Font
*Assistant Examiner*—Jason D. Vierra-Eisenberg
*Attorney, Agent, or Firm*—Sughrue, Mion, Zinn, Macpeak & Seas, PLLC

[57] ABSTRACT

A method of determining the content of insolubles in oils using (a) a relation for measuring either absorbance or transmittance from the intensity of transmitted light, (b) a calibration curve for determining the content of insolubles on calibration curve in an oil sample of interest from a measured intensity of scattered light as obtained with a standard sample, (c) the first correlationship for determining the first coefficient of quantification for correcting the effects of the color intensity of the oil sample and the content of insolubles in it, and (d) the second correlationship for determining the second coefficient of quantification for correcting the effects of the particle size distribution of the insolubles and an apparatus for determining the content of insolubles in oils including basically a light source, an interference filter, a sample cell, a measuring device for the intensities of scattered and transmitted components from a sample, a computing unit for performing processing operations based on the correcting procedures, and a sample cell holder.

12 Claims, 12 Drawing Sheets

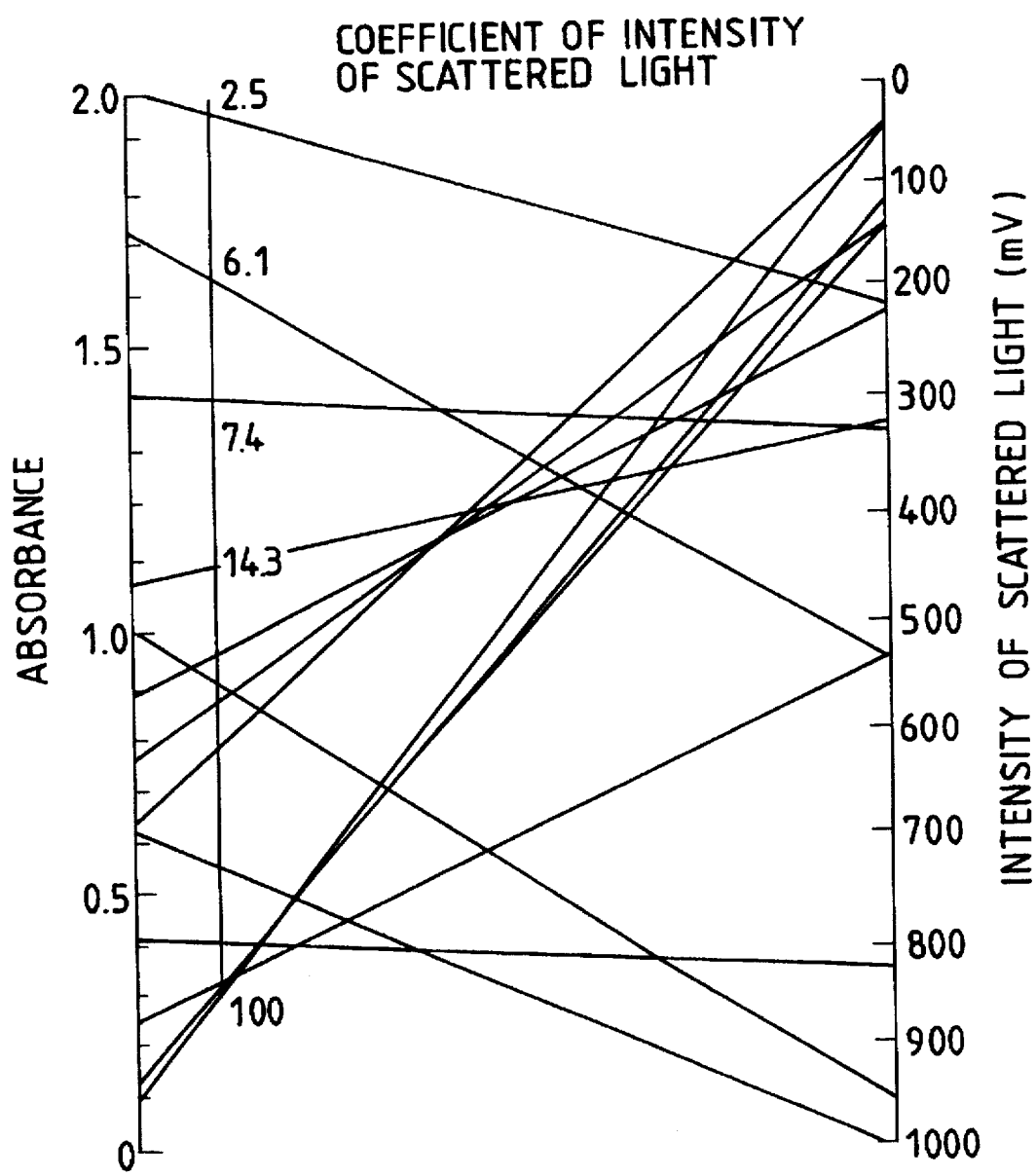

— ♦ — ENTIRE WAVELENGTH (λ) RANGE
— ● — LONG WAVELENGTH (λ) RANGE
— ✳ — SHORT WAVELENGTH (λ) RANGE

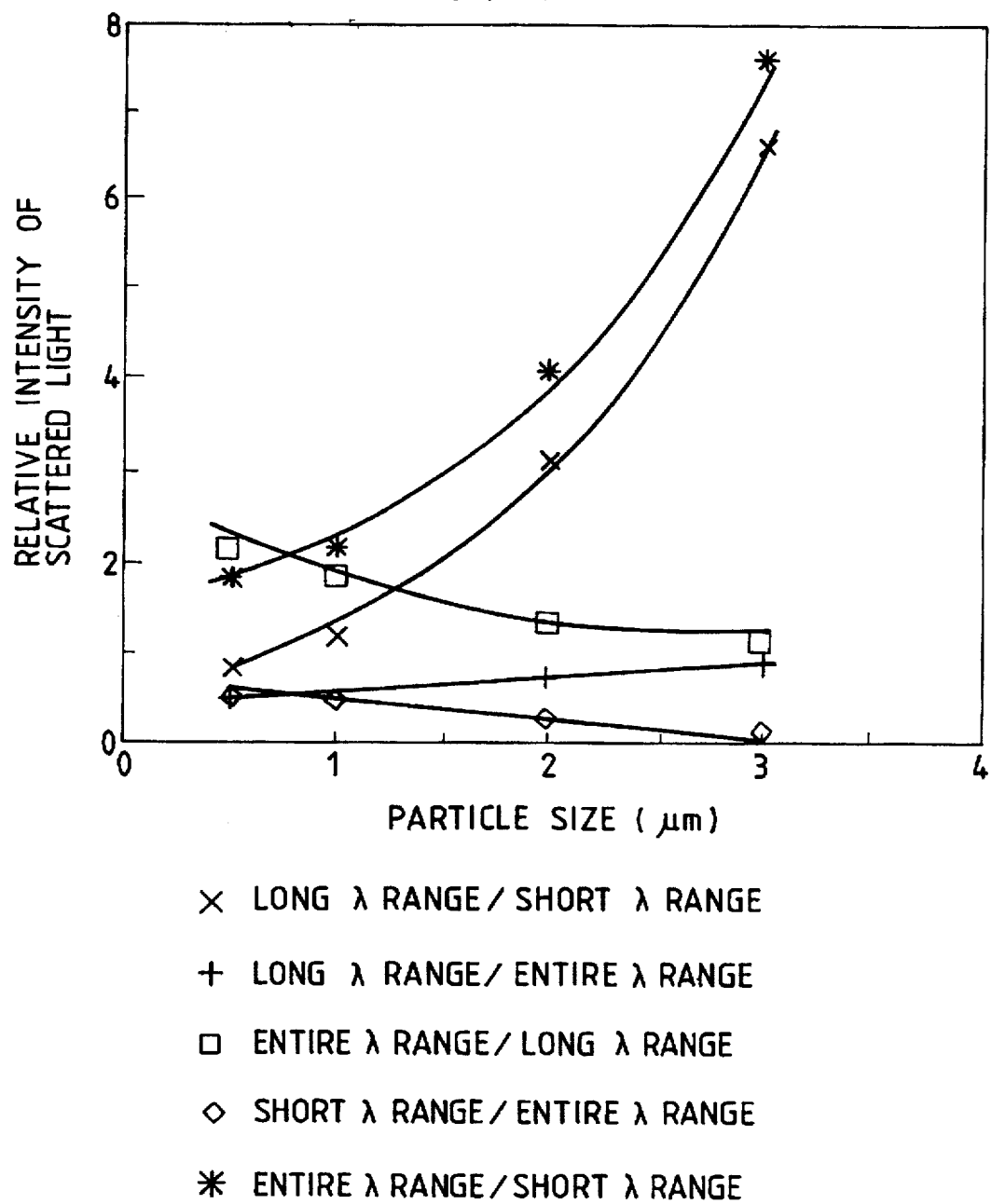

METHOD AND APPARATUS FOR DETERMINING THE CONTENT OF INSOLUBLES IN OILS

FIELD OF THE INVENTION

The present invention relates to a method and an apparatus for determining the content of insolubles in oils. More particularly, the present invention relates to a method and an apparatus that are capable of rapid and correct determination of the contents of the insolubles in oils, such as asphaltene and sludge in residual fuel oils or sludge in lubricants, as compensated for the effects of color intensity, the relative proportions of the insolubles and the size of their particles.

BACKGROUND OF THE INVENTION

Asphaltene which constitutes a class of the insolubles in residual fuel oils can affect the combustibility and storage stability of the oils.

In addition, sludge forms more or less in various mineral oils, in particular residual fuel oils such as hydrocracked oils. The term "sludge" is generally understood to be the matter that is retained on filter paper after heated oil is passed through the filter paper under suction.

The cause of sludge formation in residual fuel oils may be explained as follows. When a residual fuel oil is not deteriorated and remains stable, the asphaltene in it forms stable micelles, which are suspended as colloids; however, when the residual fuel oil is affected chemically such as by oxidation or thermally such as by heating, the property asphaltene changes to upset the balance of micelles, whereupon they coagulate and sediment into larger particles. This phenomenon is called the deterioration or reduced stability of the residual fuel oil. Sludge, on the other hand, derives from highly condensed aromatics in the residual fuel oil; if they change in properties due to chemical or thermal effects, the otherwise stable micelles disintegrate and coagulate to form solid or semisolid matter. Thus, the asphaltene and sludge share the common feature of being the insolubles in oil but the sludge is a separate entity from the asphaltene and exhibit different properties from them.

If residual fuel oils contain asphaltene or experience sludge formation, these oil-insolubles present various problems with the quality of the residual fuel oils, as discussed specifically below with particular reference to sludge in oil. If a residual fuel oil containing sludge is used as a fuel in combustors such as an internal combustion engine and a heating furnace, it often becomes difficult to ensure stable operation of the combustor. This is because the sludge deposits on the burner tip at the distal end of the oil burner and the plugged burner tip is no longer capable of achieving consistent combustion; alternatively, the sludge often plugs the strainer on the fuel oil pipe to instabilize the supply of the fuel oil.

It is therefore necessary to take a remedial action for removing sludge as soon as it has formed in residual fuel oils and, to this end, determining the content of sludge which is one of the insolubles in residual fuel oils correctly and rapidly and taking the necessary action is important to the quality control of residual fuel oils, particularly for the purpose of evaluating their stability or deterioration.

Two methods have heretofore been proposed for determining the amount of sludge in residual fuel oils and they are the determination of the amount of sediments in residual fuel oils (ISO 10307-1) and the dual wavelength spectrophotometry.

According to the method of determining the amount of sediments in residual fuel oils specified in ISO 10307-1 (which is hereunder abbreviated as "the weight method" for the sake of convenience), filter paper is set on a filter unit equipped with a dual heating jacket and the whole part of the filter unit is heated at 100° C. and, thereafter, an oil sample is poured over the filter paper and suction is applied until no detectable oil remains on the filter paper; subsequently, the solid or semisolid substance trapped on the filter paper is washed with n-heptane and the residue is dried for a specified time; the dried residue is weighed and the measured value is taken as indicative of the content of sludge in the oil sample.

The two-wavelength absorptiometric method is described in Unexamined Japanese Patent Publication No. Hei. 2-49141; according to this method, the residual fuel oil to be determined is preconditioned to form a film having a thickness in the range from about 0.01 mm to 5 mm; two wavelengths that are selected from the wavelength range of 500–1000 nm and that have different wavelengths are applied to the oil and the absorbance of each wavelength is measured; according to the relation between the sludge content and the absorbance of each of two wavelengths having known wavelengths, the content of sludge in the residual fuel oil is determined on the basis of the measured values of absorbance at the two selected wavelengths.

However, these conventional methods of determining the content of sludge in residual fuel oil have not fully met the demand of residual fuel oil production and storage sites for correct and rapid determination of the sludge content of oils, and the reasons are as follows.

The weight method involves cumbersome procedures and it takes about two hours to analyze the sludge content of one oil sample; in addition, highly skilled analyzing personnel is required for successful implementation of this method. Hence, the demand for performing real-time or on-time analysis at the site cannot be satisfied. Furthermore, highly viscous residual fuel oils cannot be analyzed by the weight method since the upper limit of the viscosity of oil samples that can be determined is 55 $mm^2/S$. Another problem is that the precision of determination decreases as repeated analyses are performed.

The two-wavelength absorptiometric method involves simple procedures and requires only short times of analysis, thereby meeting the demand for performing real-time or on-time analysis at the site. However, the detection limit is not lower than 0.1%.

SUMMARY OF THE INVENTION

An object of the present invention is to provide a method that is sensitive (i.e., with a lower detection limit) and which is capable of correct, rapid and simple determination of the content of the insolubles such as sludge in oils, as compensated for the effects of color intensity of an oil sample, the relative proportions of the insolubles and the size of their particles.

Another object of the present invention is to provide an apparatus for implementing the method.

The term "transmitted light value" as used herein means either absorbance or transmittance in transmitted light.

The term "the content of the insolubles" as used herein is defined by the following equation:

Insolubles content (%)=[(Net mass of the insolubles in oil (as dried))/(mass of the oil containing the insolubles)] ×100.

Similarly, the term "the content of sludge" as used herein is defined by:

Sludge content (%)=[(Net mass of the sludge in oil (as dried))/(mass of the oil containing the sludge)]×100.

The first object of the present invention can be attained by a method including the steps of:

(a) preliminarily constructing a calibration curve for determining the content of insolubles in an oil sample from a measured intensity of scattered light as obtained by incidence into a standard sample;

(b) preliminarily establishing the first correlationship by which the first coefficient of quantification for correcting errors in the determination of the content of insolubles that are caused by the color intensity of the oil sample and the relative proportion of the insolubles [the first coefficient of quantification being expressed as {(the content of insolubles on calibration curve)/(the content of insolubles as determined by the weight method)×100}] is determined on the basis of a measured transmitted light value and a measured intensity of scattered light as obtained for the oil sample;

(c) selecting any two light components of different wavelength ranges from among light that is emitted from a light source and which has longer wavelengths than a specified value in the entire wavelength range of the light source, light having shorter wavelengths than the specified value, and light of the entire wavelength range as emitted from the light source, applying the two light components of the selected wavelength ranges to the oil sample to measure the intensity of scattered light and the transmitted light value for each light component, determining the first coefficient of quantification from the first correlationship on the basis of the measured values, correcting the measured intensity of scattered light by the first coefficient of quantification to calculate the intensity of scattered light for each of the selected wavelength ranges, and preliminarily establishing the second correlationship by which the second coefficient of quantification for correcting errors in the determination of the content of insolubles that are caused by the difference in particle size [the second coefficient of quantification being expressed as (the content of insolubles as corrected for the intensity of transmitted light, or the content of insolubles as obtained by correcting the content of insolubles on calibration curve with the first coefficient of quantification)/(the content of insolubles as determined by the weight method)×100] is determined on the basis of the relative intensity of scattered light as calculated from the calculated intensities of scattered light for the two selected wavelength ranges;

(d) measuring the intensity of scattered light and the transmitted light value for the oil sample, determining the content of insolubles from the calibration curve on the basis of the measured intensity of scattered light, determining the first coefficient of quantification in accordance with the first correlationship on the basis of the measured intensity of scattered light and the measured transmitted light value, and correcting the content of insolubles on calibration curve by the first coefficient of quantification so as to calculate the content of insolubles in the oil sample that has been corrected for the intensity of transmitted light; and (e) measuring the relative intensity of scattered light from the oil sample using the light components of the two selected wavelength ranges which define the second correlationship determined in step (c), calculating the second coefficient of quantification in accordance with the second correlationship on the basis of the thus measured relative intensity of scattered light, and correcting by the second coefficient of quantification the content of insolubles in the oil sample that has been corrected for the intensity of transmitted light, so as to calculate the content of insolubles in the oil sample that has been subjected to the correction for both the intensity of transmitted light and the particle size.

The second object of the present invention can be attained by an apparatus including:

optics for applying incident light to a sample cell that has a light source and a detachably mounted filter with which a light component that is emitted from the light source and that has longer wavelengths than a specified value is applied to the sample cell;

a plurality of measuring devices for the intensities of scattered and transmitted light components emerging from the sample cell; and a calculating unit connected to the measuring device; the calculating unit being stored with:

(a) a relation for measuring the absorbance or transmittance from the intensity of transmitted light;

(b) a calibration curve for determining the content of insolubles on calibration curve in an oil sample from the intensity of scattered light as obtained for a standard sample;

(c) the first correlationship by which the first coefficient of quantification [which is expressed as (the content of insolubles on calibration curve)/(the content of insolubles as determined by the weight method)× 100] is determined on the basis of a measured transmitted light value and a measured intensity of scattered light for the oil sample; and (d) the second correlationship by which the second coefficient of quantification [which is expressed as (the content of insolubles as corrected for the intensity of transmitted light, or the content of insolubles as obtained by correcting the content of insolubles on calibration curve with the first coefficient of quantification)/(the content insolubles as determined by the weight method)×100] is determined on the basis of the relative intensity of scattered light as calculated from the intensities of scattered light for two selected wavelength ranges that have been measured by the steps of selecting any two light components of different wavelength ranges from among light that is emitted from the light source and which has longer wavelengths than a specified value in the entire wavelength range of the light source, light having shorter wavelengths than the specified value, and light of the entire wavelength range as emitted from the light source, applying the two light components of the selected wavelength ranges to the oil sample to measure the intensity of scattered light and the transmitted light value for each light component, determining the first coefficient of quantification from the first correlationship on the basis of the measured values, and correcting the measured intensity of scattered light by the first coefficient of quantification to calculate the intensity of scattered light for each of the selected wavelength ranges.

BRIEF DESCRIPTION OF THE DRAWINGS

FIG. 7 is a diagram showing how to construct a nomograph representing the relationship between the absorbance, the intensity of scattered light and the coefficient of quantification of scattered light;

FIG. 16 is a graph showing how various relative intensities of scattered light correlate to the particle size.

DETAILED DESCRIPTION OF THE INVENTION

In the course of their R&D efforts to offer the desired method and apparatus for determining the contents of the insolubles in oils, the present inventor noted on the optical determination of the content of insolubles in oils and confirmed by experimentation the following, which is hereunder described with reference to sludge taken for illustrative purposes only.

First, it was confirmed that the content of sludge in residual fuel oils could be determined optically, or stated more specifically, by applying incident light to the sludge-containing residual fuel oil and measuring the intensity of emerging scattered light. The process started with preparing standard samples of various known values of sludge content from a hydrocracked residual fuel oil. Specifically, a residual fuel oil containing a large amount of sludge was filtered by the weight method and an undiluted residual fuel oil was diluted with the filtered oil as appropriate for preparing standard samples of varying sludge contents. The intensities of scattered light from the standard samples and their absorbances were measured with a turbidimeter (Model UT-11 of Corona Denki K. K. capable of measuring the intensities of scattered and transmitted light components) and the relationship of the sludge content and the intensity of scattered light was determined for the individual standard samples. The results are shown in FIG. 13.

Figure 13:
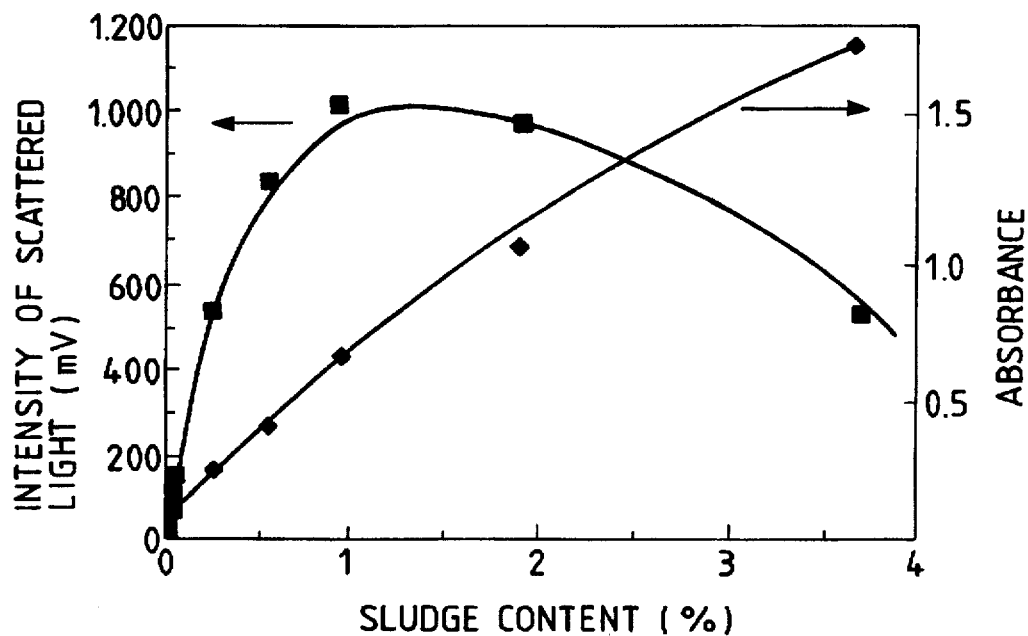
FIG. 13 is a graph showing the relationship between the sludge content of standard samples and each of measured values of the intensity of scattered light and the absorbance.

The data shown in FIG. 13 revealed that when the oil transmitted a small amount of light, the sludge content had a linear correlationship with the intensity of scattered light in a low-sludge region. As is clear from FIG. 5 which shows enlarged the low-sludge region of FIG. 13, the correlationship between the sludge content and the intensity of scattered light is substantially linear and expressed by a straight line in the region where the sludge content is less than 0.15%, and the intensity of scattered light tends to become lower than the straight line as the sludge content increases.

Figure 5:
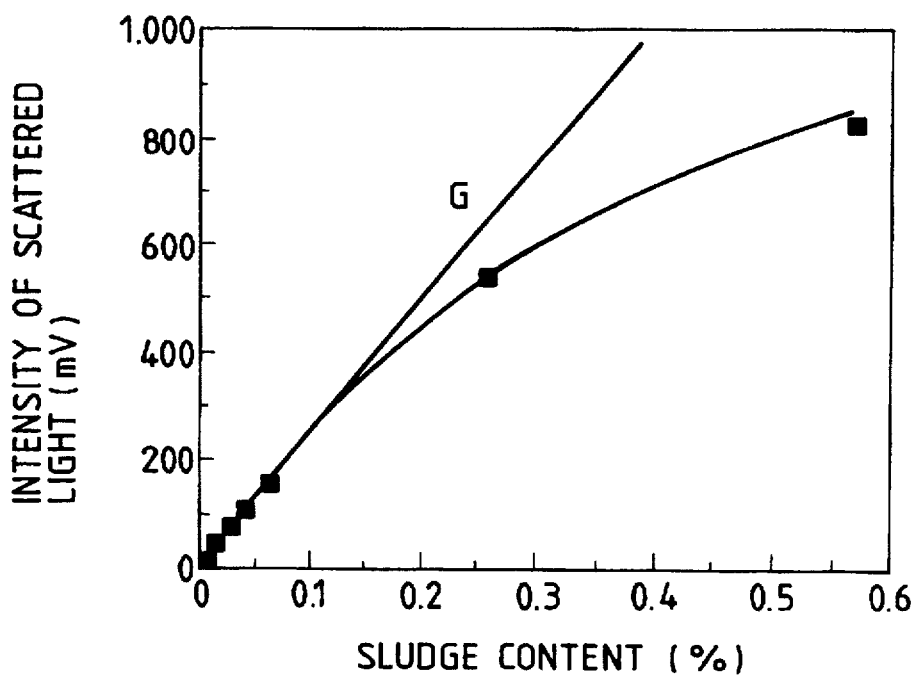
FIG. 5 is a graph showing calibration curve G.

Based on this finding, the present inventor thought it to be instrumental to use the straight line in FIG. 5 and its extension as a calibration curve which represents the correlationship between the sludge content and the intensity of scattered light (which may be regarded as the line representing 100% of the first coefficient of quantification, infra).

Secondly, the present inventor analyzed the effects of the color intensity of standard samples on the determination of sludge content. In the analysis, a sample cell filled with a standard sample of a known sludge content that transmitted a large intensity of light was placed in series with a sample cell filled with a sludge-free standard sample that transmitted a small intensity of light (i.e., a residual fuel oil prepared by atmospheric distillation of a crude); incident light was applied to the two cells and the intensities of scattered and transmitted light components were measured with a turbidimeter and the resulting data were used as the intensities of scattered and transmitted light components from the colored standard sample.

In this way, colored standard samples with different known values of sludge content were measured for the intensity of scattered light and the absorbance. The results were expressed as the measured values for the intensity of scattered light and the absorbance vs the sludge content of the colored standard samples and they are shown in FIG. 6.

Figure 6:
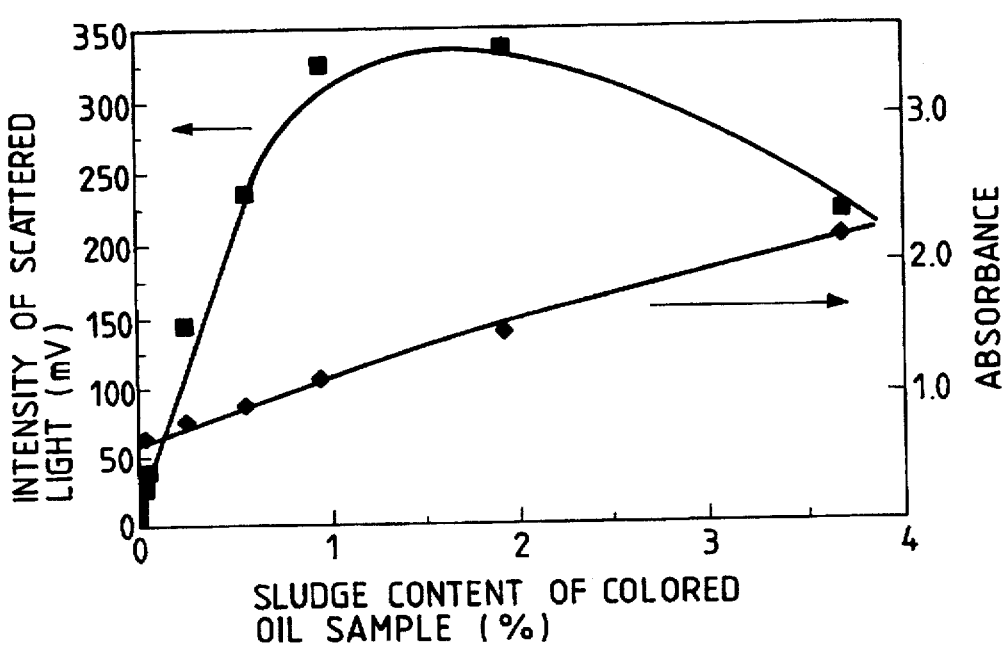
FIG. 6 is a graph showing the relationship between the sludge content of a colored oil sample, the intensity of scattered light and the absorbance.

The experimental data shown in FIGS. 6 and 13 revealed that given the same sludge content, the intensity of scattered light and the absorbance in the case where the color intensity of oil was constant but the sludge content was variable differed from those in the case where the intensity of oil color was increased. FIGS. 6 and 13 show variances of the intensity of scattered light and the absorbance in the cases where the color intensity of oil was constant but the sludge content was variable and where the color intensity of oil was increased but the sludge content was variable, respectively. Thus it has been found that the intensity of scattered light and the absorbance were affected by both of the color intensity of oil and the sludge content. Considering the fact that absorbance is a factor more directly variable with the color intensity of oil and the relative proportion of sludge than the intensity of scattered light, the present inventor assumed that errors in the determination of sludge content due to the color intensity and the relative proportion of sludge could possibly be corrected by the differences in absorbance and the intensity of scattered light which are shown in FIGS. 6 and 13.

Figure 14:
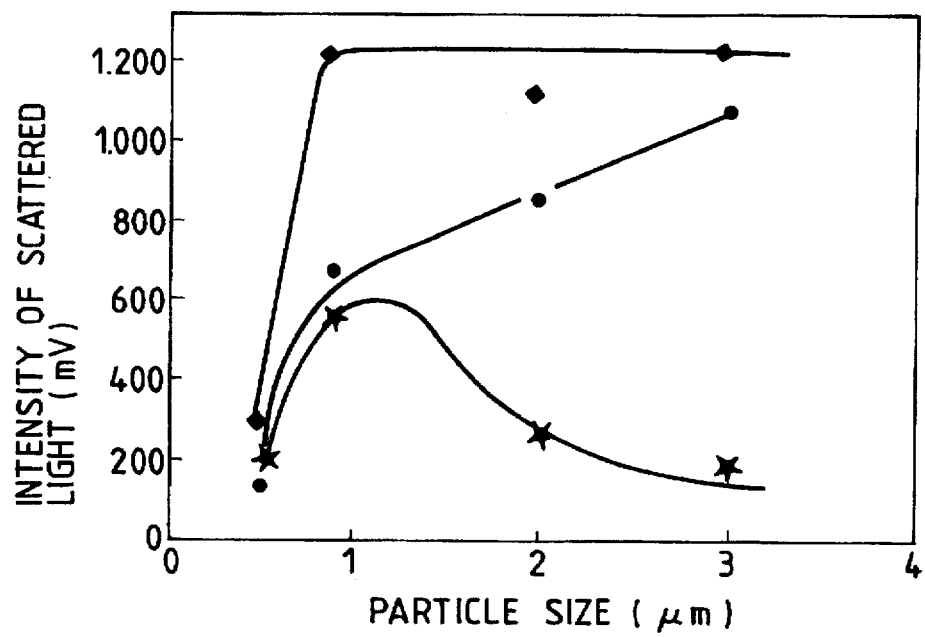
FIG. 14 is a graph showing the relationship between the particle size and the intensity of scattered light for different spectra of light.
Figure 15:
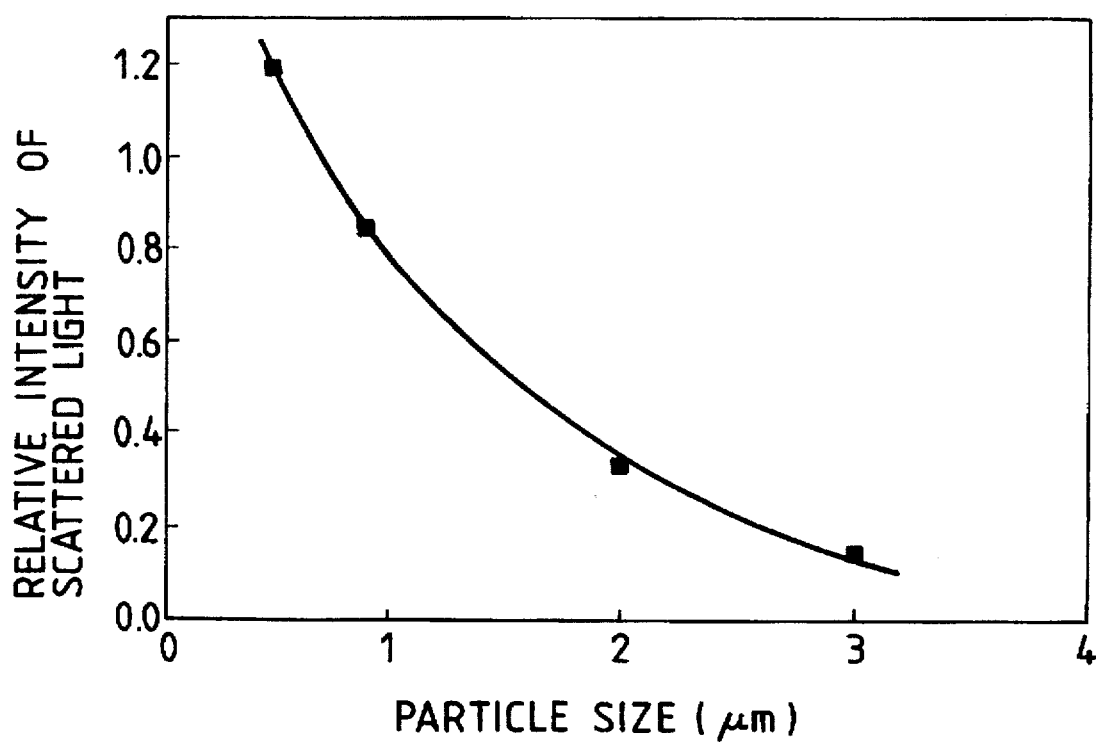
FIG. 15 is a graph showing the relationship between the particle size and the relative intensity of scattered light.

Thirdly, the present inventor analyzed the effects of the average size of sludge particles on the determination of sludge content. Noting that the intensity of scattered light was variable with the wavelength of incident light even when the sludge content and the sludge particle size were of the same values, the present inventor prepared colorless standard samples with known values of sludge content by mixing oil with solid particles of a known size, for example, commercial standard solid particles in various amounts, say, 0–5.0%, and by then applying two light components of different wavelength ranges so as to measure the intensity of scattered light from the samples. The results were as shown in FIGS. 14 and 15.

The two light components were light of the entire wavelength range emitted from a tungsten lamp and light of longer wavelengths than 700 nm as obtained with an interference filter that would block light of the shorter wavelengths. The data shown in FIG. 14 as representing the intensity of scattered light in a short wavelength range were obtained by subtracting the values for the intensity of light scattered by particles of the same size upon incidence of light of the long wavelength range from the values for the intensity of light scattered by particles of the same size upon incidence of light of the entire wavelength range.

The label "relative intensity of scattered light by wavelength range" on the vertical axis of the graph in FIG. 15 (which is hereunder abbreviated simply as the "relative intensity of scattered light") means the ratio of the intensity of scattered light of the short wavelength range to that of the long wavelength range for the same particle size and may be expressed as follows:

Relative intensity of scattered light=(Intensity of scattered light in short wavelength range)/(intensity of scattered light in long wavelength range)

FIG. 15 shows that the relative intensity of scattered light has a certain relationship with the particle size.

It has also been found that the relative intensity of scattered light need not be the ratio associated with the short and long wavelength ranges but that it may be measured with any two light components in different wavelength ranges, namely, light that is emitted from a light source and which has longer wavelengths than a specified value in the entire wavelength range of the light source, light having shorter wavelengths than the specified value, and light of the entire wavelength range as emitted from the light source. Thus, according to the present invention, two light components of selected wavelength ranges are each applied to an oil sample to measure the intensity of scattered light and the absorbance; then, the first coefficient of quantification is calculated from the first correlationship on the basis of the measured values, and the measured intensity of scattered light is corrected by the first coefficient of quantification so as to calculate the intensities of scattered light in the two light components of the selected wavelength ranges, from which the relative intensity of scattered light is measured.

Hence, the relative intensity of scattered light can be expressed in the following six ways: a corrected intensity of scattered light of the short wavelength range (hereunder referred to simply as "short wavelength")/a corrected intensity of scattered light of the long wavelength range (hereunder referred to simply as "long wavelength"), long wavelength/short wavelength, short wavelength/a corrected intensity of scattered light of the entire wavelength range (hereunder referred to as "entire wavelength"), entire wavelength/short wavelength, long wavelength/entire wavelength, and entire wavelength/long wavelength, and any of these expressions can be used as the relative intensity of scattered light in the present invention.

These relative intensities of scattered light correlate with the particle size as shown in FIG. 16.

The present invention has been accomplished on the basis of the results of the studies described above and its first object can be attained by a method of determining the contents of the insolubles in oils, which includes the steps of:

(a) preliminarily constructing a calibration curve for determining the content of insolubles in an oil sample from a measured intensity of scattered light as obtained by applying incident light to a standard sample;

(b) preliminarily establishing the first correlationship by which the first coefficient of quantification for correcting errors in the determination of the content of insolubles that are caused by the color intensity of the oil sample and the relative proportion of the insolubles [the first coefficient of quantification being expressed as {(the content of insolubles on calibration curve)/(the content of insolubles as determined by the weight method)×100}] is determined on the basis of a measured transmitted light value and a measured intensity of scattered light as obtained for the oil sample;

(c) selecting any two light components of different wavelength ranges from among light that is emitted from a light source and which has longer wavelengths than a specified value in the entire wavelength range of the light source, light having shorter wavelengths than the specified value, and light of the entire wavelength range as emitted from the light source, applying the two light components of the selected wavelength ranges to the oil sample to measure the intensity of scattered light and the transmitted light value for each light component, determining the first coefficient of quantification from the first correlationship on the basis of the measured values, correcting the measured intensity of scattered light by the first coefficient of quantification to calculate the intensity of scattered light for each of the selected wavelength ranges, and preliminarily establishing the second correlationship by which the second coefficient of quantification for correcting errors in the determination of the content of insolubles that are caused by the difference in particle size [the second coefficient of quantification being expressed as (the content of insolubles as corrected for the intensity of transmitted light, or the content of insolubles as obtained by correcting the content of insolubles on calibration curve with the first coefficient of quantification)/(the content of insolubles as determined by the weight method)×100] is determined on the basis of the relative intensity of scattered light as calculated from the calculated intensities of scattered light for the two selected wavelength ranges;

(d) measuring the intensity of scattered light and the transmitted light value for the oil sample, determining the content of insolubles from the calibration curve on the basis of the measured intensity of scattered light, determining the first coefficient of quantification in accordance with the first correlationship on the basis of the measured intensity of scattered light and the measured transmitted light value, and correcting the content of insolubles on calibration curve by the first coefficient of quantification so as to calculate the content of insolubles in the oil sample that has been corrected for the intensity of transmitted light; and (e) measuring the relative intensity of scattered light from the oil sample using the light components of the two selected wavelength ranges which define the second correlationship determined in step (c), calculating the second coefficient of quantification in accordance with the second correlationship on the basis of the thus measured relative intensity of scattered light, and correcting by the second coefficient of quantification the content of insolubles in the oil sample that has been corrected for the intensity of transmitted light, so as to calculate the content of insolubles in the oil sample that has been subjected to the correction for both the intensity of transmitted light and the particle size.

The second object of the present invention can be attained by an apparatus for determining the content of the insolubles in oils, which includes:

optics for applying incident light to a sample cell that has a light source and a detachably mounted filter with which a light component that is emitted from the light source and that has longer wavelengths than a specified value is applied to the sample cell;

a plurality of measuring devices for the intensities of scattered and transmitted light components emerging from the sample cell; and a calculating unit connected to the measuring device;

the calculating unit being stored with:

(a) a relation for measuring the absorbance or transmittance from the intensity of transmitted light;

(b) a calibration curve for determining the content of insolubles on calibration curve in an oil sample from the intensity of scattered light as obtained for a standard sample;

(c) the first correlationship by which the first coefficient of quantification [which is expressed as (the content of insolubles on calibration curve)/(the content of insolubles as determined by the weight method)× 100] is determined on the basis of a measured transmitted light value and a measured intensity of scattered light for the oil sample; and (d) the second correlationship by which the second coefficient of quantification [which is expressed as (the content of insolubles as corrected for the intensity of transmitted light, or the content of insolubles as obtained by correcting the content of insolubles on calibration curve with the first coefficient of quantification)/(the content of insolubles as determined by the weight method)×100] is determined on the basis of the relative intensity of scattered light as calculated from the intensities of scattered light for two selected wavelength ranges that have been measured by the steps of selecting any two light components of different wavelength ranges from among light that is emitted from the light source and which has longer wavelengths than a specified value in the entire wavelength range of the light source, light having shorter wavelengths than the specified value, and light of the entire wavelength range as emitted from the light source, applying the two light components of the selected wavelength ranges to the oil sample to measure the intensity of scattered light and the transmitted light value for each light component, determining the first coefficient of quantification from the first correlationship on the basis of the measured values, and correcting the measured intensity of scattered light by the first coefficient of quantification to calculate the intensity of scattered light for each of the selected wavelength ranges.

The filter to be used in the present invention is in way limited as long as light components having shorter wavelengths than a specified wavelength can be blocked. For example, an interference filter may be employed as will be described in the Example that follows. The "specified wavelength" as mentioned herein may be selected at any value but it is preferably such that the intensity of light in the wavelength range shorter than the specified value is almost equal to the intensity of light in the longer wavelength range; for example, 700 nm may be selected as the specified wavelength as will be described in the Example that follows.

The results of measurement of the intensities of scattered light from three samples that differed in the size of sludge particles are shown in Table 1. As shown, the intensity of light in the shorter wavelength range is measured from the intensities of light in two wavelength ranges and the relative intensity of scattered light can in turn be measured as the ratio between the long and short wavelength ranges. Obviously, the relative intensity of scattered light varies with the size of sludge particles, it is also clear from Table 1 that when 700 nm is taken as the "specified value" that separates the long and short wavelength ranges, the relative intensity of scattered light varies from 0.3 to 0.8.

TABLE 1

| Sample | Intensity of scattered light over the entire wavelength range, mV | Intensity of scattered light in the long wavelength range (>700 nm), mV | Intensity of scattered light in the short wavelength range (≦700 nm), mV | Relative intensity of scattered light |
|---|---|---|---|---|
| A | 100 | 57 | 43 | 0.75 |
| B | 100 | 68 | 32 | 0.47 |
| C | 100 | 73 | 27 | 0.37 |
| Method of measurement | actual measurement | actual measurement | (Entire)- (>700) | (short/ long) |

Note:
The expression "(entire)-(>700)" in the row of "method of measurement" means that the intensity of scattered light in the wavelength range longer than 700 nm is subtracted from the intensity of light over the entire wavelength range.

The entire wavelength range is from 100 to 1000 nm and, considering the particle size of insolubles, the range is preferably from 350 to 1000 nm. Any light sources can be used as long as they cover these wavelength ranges and a tungsten lamp is used with advantage. The scattering with the insolubles in oils is to be measured over the entire wavelength range. Since the intensity of scattered light by wavelength depends on the particle size, the relative intensity of scattered light varies with the particle size. Therefore, the relationship between the particle size and the relative intensity of scattered light can be determined even if wavelengths other than 700 nm are taken as the "specified value" that separates the long and short wavelength ranges. For precise determination, the relative intensity of scattered light ranges from 9/1 to 1/9, so the "specified value" that separates the two wavelength ranges is between 200 and 950 nm.

The optical pathlength of the light that is transmitted through the oil sample is the cause of errors irrespective of whether it is unduly long or short; if it is unduly long, increased absorbance reduces the intensity of scattered light and if it is unduly short, both the absorbance and the intensity of scattered light decrease. Therefore, an appropriate optical pathlength ranges from 0.01 to 10 mm and, considering the effect of the color intensity of samples, a preferred optical pathlength is from 0.05 to 0.5 mm, with values about 0.1 mm being more preferred. Hence, as will be described in the Example that follows, it is recommended to provide a sample cell with a groove 0.1 mm deep, which is to be filled with an oil sample of interest.

The calibration curve, the first correlationship and the second correlationship are preliminarily determined by experimentation as will be described in the Example which follows.

The method of the present invention is applicable irrespective of the type of oils and the properties of the insolubles in the oils but it can be applied with particular advantage under the conditions to be set forth below. Specifically, the method is applicable to the purpose of determining the contents of asphaltene and sludge in residual fuel oils, or the relative proportion of insolubles contained in lubricants. If oils to be analyzed contain large amounts of sludge and other insolubles, they may be diluted as appropriate for the specific determination.

If the content of asphaltene is to be determined, it is necessary that an aromatic hydrocarbon such as benzene, toluene or xylene by added to an oil sample of interest and, after a complete solution forms, an aliphatic hydrocarbon such as pentane, hexane, heptane or octane be added to precipitate the asphaltene before actual analysis is started.

Density of oil: 0.8–1.1 g/cm$^3$

Content of insolubles: 0.01–5%

Average particle size of insolubles: 0.5–5 μm

Color intensity: ca. 2 in absorbance (D 8.0 Dil under ASTM color designation)

Light source: tungsten lamp (without spectral distribution)

According to the present invention, the intensity of scattered light is measured and the content of insolubles is determined on the calibration curve from a measured intensity of scattered light; further, the first coefficient of quantification is determined in accordance with the first correlationship on the basis of the measured intensity of scattered light and a measured transmitted light value and, then, the content of insolubles on calibration curve is corrected by the first coefficient of quantification to calculate the content of insolubles as corrected for the intensity of transmitted light. Furthermore, the relative intensity of scattered light is calculated by a specified procedure and the second coefficient of quantification is calculated on the basis of the calculated relative intensity of scattered light. The content of insolubles that has been corrected for the intensity of transmitted light is further corrected by the calculated second coefficient of quantification so as to calculate the content of insolubles that has been corrected for both the intensity of transmitted light and the particle size.

Performed in this way, the method of the present invention offers the following advantages: first, the content of insolubles can be determined as the correct value that has been compensated for the errors of determination due to the color intensity of an oil sample, the relative proportion of insolubles and its particle size; secondly, the method of the present invention has a sufficiently low detection limit to enable determination on oil samples having low content of insolubles; thirdly, the parameters to be determined by the method of the present invention have such high reproducibility that the results of determinations are subject to less personal errors and insure higher precision than the conventional weight method which involves filtration the weighing steps; fourthly, the method of the present invention requires only simple procedures and can complete the intended analysis within a short time.

In addition, the method of the present invention is applicable to the test for evaluating the heat stability of residual fuel oils. The principle of determination by this method is also applicable to the determination of the solvent-insolubles in lubricants. Therefore, by applying the method of the present invention to these tests, the objective of testing can be attained in a much shorter time and with a simpler apparatus than the prior art methods and yet with comparable precision to the latter.

The method of the present invention for determining the content of the insolubles in oils includes optics for applying incident light to a sample cell that has a light source and a detachably mounted filter with which a light component that is emitted from the light source and that has longer wavelengths than a specified value is applied to the sample cell, a plurality of measuring devices for the intensities of scattered and transmitted light components emerging from the sample cell, and a calculating unit connected to the measuring device. The arrangement of these parts insures that the content of insolubles can be calculated as the correct value that has been compensated for the errors of determination due to the color intensity of the oil sample, the relative proportion of insolubles and its particle size and, what is more, this can be accomplished by simple procedures in a rapid way.

The apparatus of the present invention can be used to determine the correct values of the content of the insolubles in oils such as asphaltene and sludge in residual fuel oils on a real-time or on-time basis.

On the pages that follow, the present invention is described in greater detail with reference to the preferred example shown in accompanying drawings.

Figure 1:
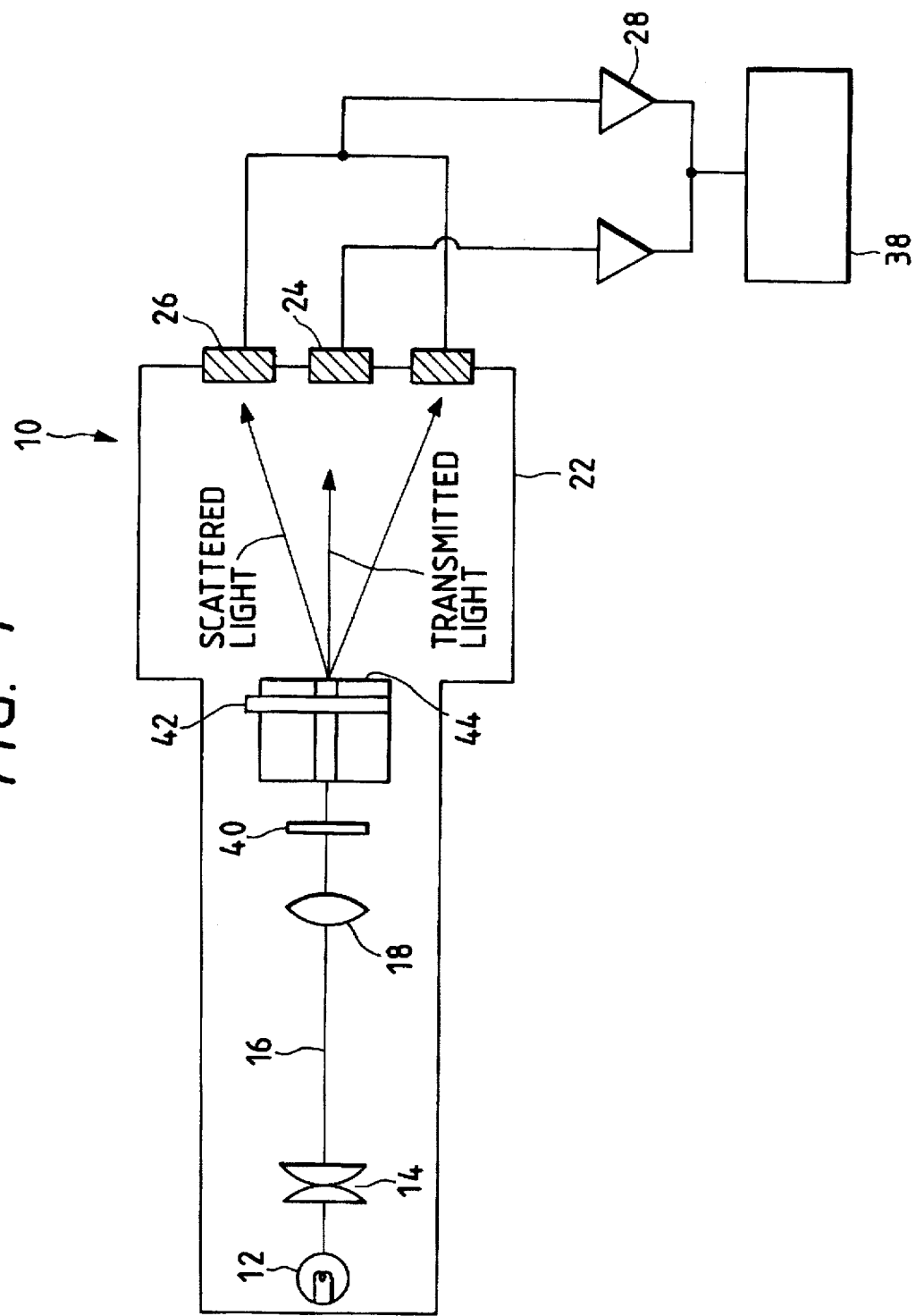
FIG. 1 shows schematically the construction of an exemplary apparatus for determining the sludge content of oil in accordance with the present invention.

FIG. 1 shows schematically the construction of an exemplary apparatus for implementing the method of the present invention in order to determine the content of insolubles. The apparatus generally indicated by 10 in FIG. 1 is an adaptation from Model UT-11 (the turbidimeter of Corona Denki K. K. capable of measuring the intensities of scattered and transmitted light components). The turbidimeter includes a light source (tungsten lamp) 12, a condenser lens 14, a pinhole 16, a collimator lens 18, a light-receiving unit 22 having both a detector of transmitted light 24 and detectors of scattered light 26, and an amplifying unit 28.

In addition to these components of the turbidimeter, the apparatus 10 has a computer 38 connected to the amplifier unit 28, an interference filter 40 provided between the collimator lens 18 and a sample cell 42, and a holder 44 for supporting the sample cell 42.

The computer 38 is a calculating unit and, in accordance with the calibration curve, the first correlationship and the second correlationship that will be described later, it can calculate the content of insolubles as corrected for the intensity of transmitted light, and the content of insolubles as corrected for both the intensity of transmitted light and the particle size of the insolubles.

Interference filter 40 as used in the example under consideration is such that only the component of incident light from the tungsten lamp 12 that has longer wavelengths than 700 nm is applied to the sample cell 42; this filter is mounted detachably.

Figure 2A:
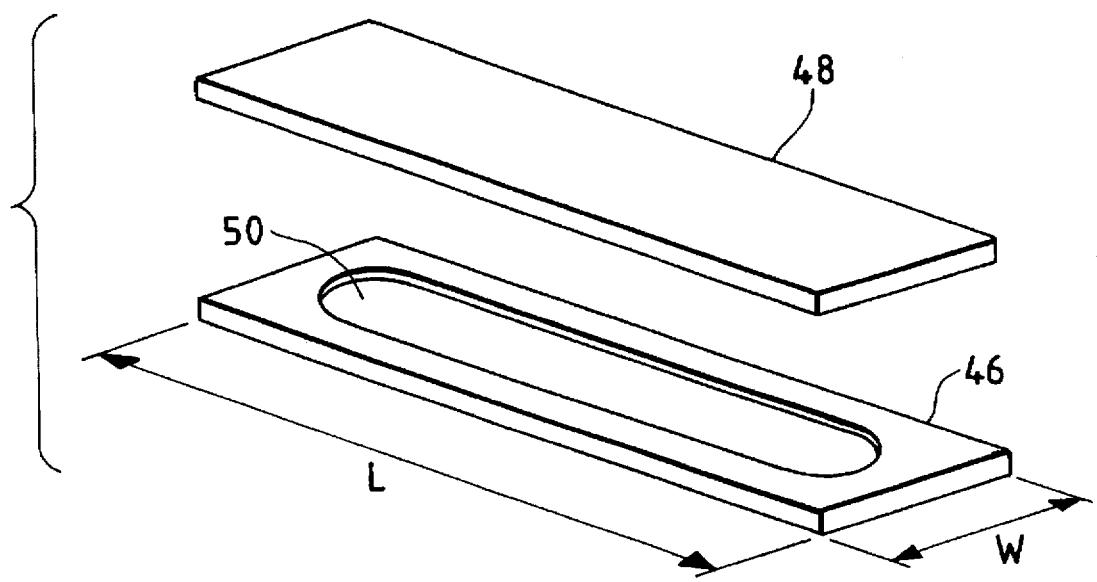
FIG. 2A is a perspective view of the sample cell in FIG. 1.
Figure 2B:
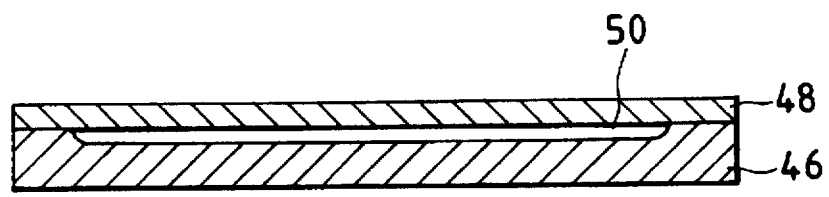
FIG. 2B is a longitudinal section of the sample cell.

As FIG. 2A shows, sample cell 42 is composed of a thin slender container 46 and a cover 48, each being made of a transparent material such as glass or silica glass. As shown in FIG. 2B, container 46 has a groove 50 formed in a depth of 0.1 mm to extend in both directions of the width (W) and length (L) of the container. When determining the content of insolubles, the groove 50 is filled with an oil sample of interest and overlaid with the cover 48, so the cell 42 has an optical pathlength of 0.1 mm. In the example under consideration, the width (W) of the container 46 is about 10 mm and its length (L) is about 40 mm.

Figure 3A:
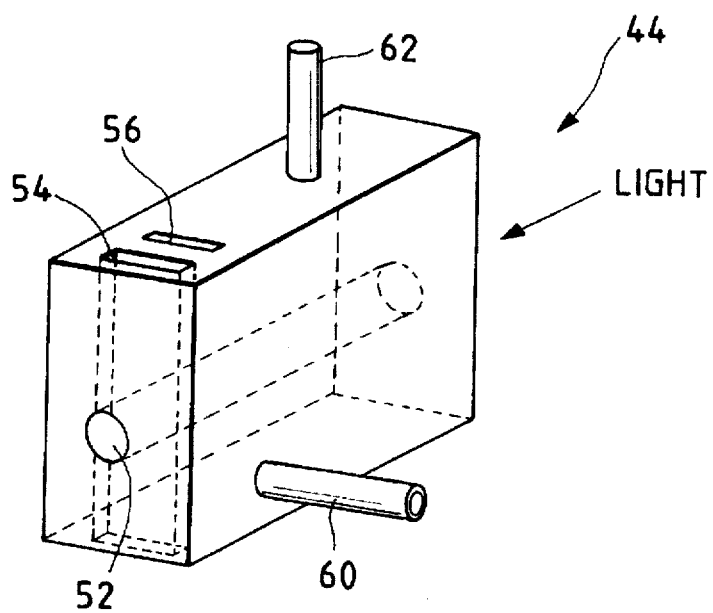
FIG. 3A is a perspective view of the sample cell holder in FIG. 1.

The sample cell holder 44 is a metallic box provided and as FIG. 3A shows, it is provided with a hole 52 having an inside diameter of about 6 mm through which light is to be passed toward the sample cell holder 44 and two slots 54 and 56 for inserting the sample cell 42.

Figure 3B:
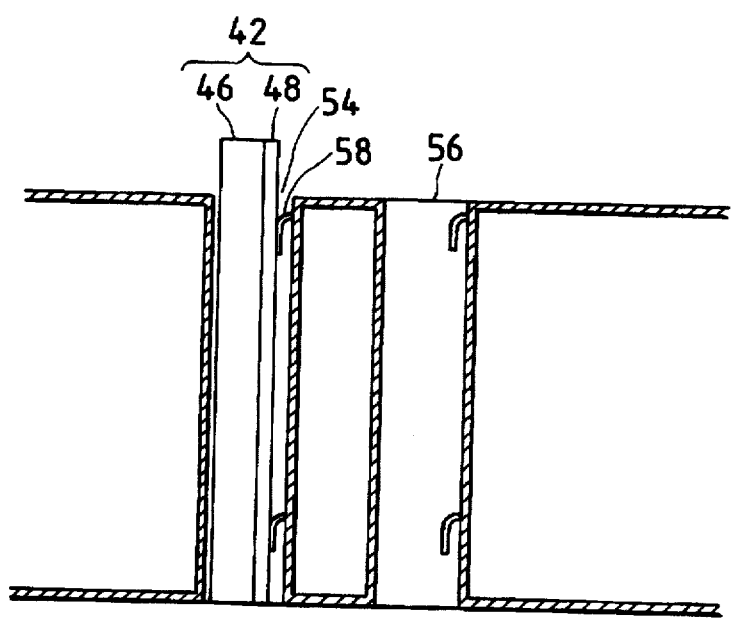
FIG. 3B is a section of the slots into which the sample cell is to be inserted.

The first slot 54 is positioned close to the exit of the light passage hole 52 and the second slot 56 is positioned close to the first slot 54. The openings of both slots have substantially the same dimensions as the external dimensions of the sample cell 42 which are illustrated in FIG. 2B and the slots are so positioned that the sample cell 42 can be inserted in such a way that the optical path of light travelling through the sample cell 42 is parallel to incident light. The first and second slots 54 and 56 are provided with leaf springs 58 in appropriate areas as shown in FIG. 3B; the springs 58 press the inserted sample cell 42 to secure the integral assembly of the container 46 of the cell 42 and its cover 48 so that the oil sample does not leak out of the groove 50. The sample cell holder 44 is connected to a warm water supply pipe 60 and a warm water drain pipe 62 such that the sample cell 42 can be heated with warm water supplied through the pipe 60.

The sample cell holder 44 is provided in contact with the entrance window in the light-receiving unit 22 and in a measuring mode, the sample cell 42 is inserted into the first slot 54 in the cell holder 44.

The apparatus 10 having this construction is operated in the following way. Light issuing from tungsten lamp 12 passes through the condenser lens 14 and pinhole 16 to converge and then passes through collimator lens 18 to form parallel rays. If the apparatus 10 is equipped with interference filter 40, only incident light having wavelengths longer than 700 nm is applied to sample cell 42 through hole 52 in the sample cell holder 44 by the interfering action of filter 40. If the apparatus 10 is not equipped with such interference filter, incident light of the entire wavelength range is applied to the sample cell 42. Part of the thus incident light is absorbed and part of the remainder is transmitted without being scattered in the sample cell 42 whereas the other part is scattered by the particles of the insolubles in the oil contained in the sample cell 42.

The light passing through the sample cell 42 is applied to the light-receiving unit 22. The transmitted light component is applied to the detector 24 whereas the scattered light component is applied to the detectors 26. The transmitted and scattered light components entering the associated detectors are measured for their intensities by those detectors, from which the measured intensities of the respective light components are delivered as corresponding output electric signals. The intensities of the respective light components which have been converted to electric signals are amplified by amplifying unit 28, thence entered into computer 38.

In accordance with the preloaded calibration curve, first correlationship and second correlationship, computer 38 calculates rapidly the content of insolubles as corrected for the intensity of transmitted light, and the content of insolubles as corrected for both the intensity of transmitted light and the particle size on the basis of a measured absorbance or transmittance, a measured intensity of scattered light and a calculated relative intensity of scattered light.

How to Construct the Calibration Curve

An example of the method of constructing the calibration curve will now be described with reference to the case of determining the content of sludge in a residual fuel oil. It should be noted that calibration curves for use in other cases such as determining the content of asphaltene in residual fuel oils or the content of insolubles in lubricants can be constructed on the basis of the weight method in accordance with the following procedure. The process starts with preparing a plurality of standard samples (i.e., thermally deteriorated hydrocracked bottoms from the atmospheric distillation of crude oil) such that they contain sludge in amounts of 0–5%; then the sludge content of each sample is determined by the weight method. As already mentioned, the standard samples are prepared by diluting a residual fuel oil of interest with a sludge-filtered oil. It should also be noted that the plurality of standard samples may be replaced by polyethylene lattices having constant particle sizes. Any particle sizes ranging from 0.1 to 100 µm may be used as the standard but it is preferred to use particles having a size distribution close to that of the insolubles to be determined. If the content of sludge is to be determined, it is preferred to use standard particles of 0.5–3 µm. Subsequently, the same standard samples are measured for the intensity of scattered light and the transmitted light value using the apparatus 10 already described above. When constructing the calibration curve, the entire wavelength range of light issuing from the tungsten lamp 12 is to be used and, hence, the apparatus 10 is not equipped with interference filter 40.

Figure 4:
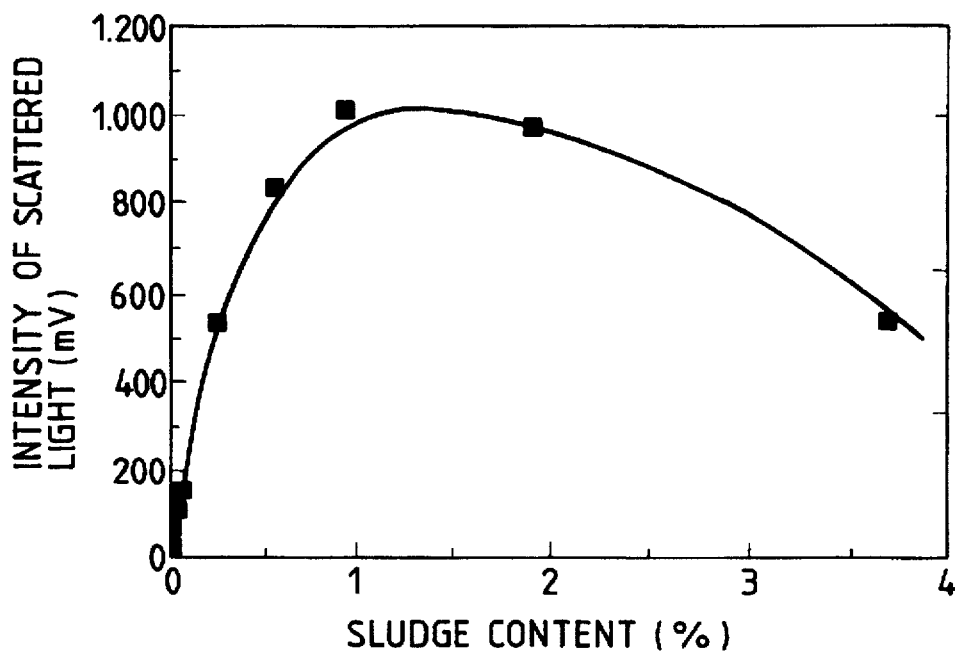
FIG. 4 is a graph showing the relationship between the sludge content and the intensity of scattered light.

The relationship between the content of sludge as determined by the weight method and the measured intensities of scattered light is shown graphically in FIG. 4, and the area of FIG. 4 where the sludge content is 0.6% and less is shown enlarged in FIG. 5. In a region of low sludge content, say, not more than about 0.2%, a linear correlationship holds between the content of sludge and the intensity of scattered light and is expressed by a straight line, which is extended to construct calibration curve G as shown in FIG. 5.

After constructing the calibration curve G, one may measure the intensity of scattered light form an oil sample of interest; then, using the calibration curve G, one can determine the content of sludge in the oil sample that corresponds to the measured intensity of scattered light. The linear correlationship shown in FIG. 5 can be represented by a numerical expression such that the sludge content per millivolt of scattered light is $6.29 \times 10^{-4}$%. The content of sludge as determined either from the calibration curve or by the stated expression is herein referred to as the "sludge content on calibration curve".

How to Establish the First Correlationship which Determines the First Coefficient of Quantification for Making Corrections for the Color Intensity and the Relative Proportion of Sludge There is now described an example of the method of establishing the first correlationship which determines the first coefficient of quantification. A sample cell containing either one of the standard samples used in constructing the calibration curve is inserted into the first slot 54 in the sample cell holder 44 in the apparatus 10; on the other hand, a sample cell containing a colored oil with a specified color intensity, for example, a residual fuel oil colored to a specified intensity, is inserted into the second slot 56 in the sample cell holder 44. Then, the intensity of scattered light and the transmitted light value of either absorbance or transmittance are measured for use as data for the colored standard sample.

In the example under consideration, absorbance is expressed as:

$$\text{Absorbance } A = \log((T_1-T_0)/(T_2-T_0)) \quad (1)$$

and transmittance is expressed as:

$$\text{Transmittance } T = ((T_2-T_0)/(T_1-T_0)) \times 100 \quad (1')$$

where $T_1$: voltage (mV) indicative of transmitted light from decane which is used as a transparent blank sample;

$T_0$: voltage (mV) indicative of transmitted light as obtained when the optical path is blocked;

$T_2$: voltage (mV) indicative of transmitted light from the standard sample.

On the basis of the transmitted light value and the intensity of scattered light that have been measured on the intensely colored standard sample and the standard samples which are constant in color intensity but varied in sludge content, the correlationship between the first coefficient of quantification (to be defined below), the transmitted light value and the intensity of scattered light (which correlationship is hereunder referred to as "the first correlationship") is established. The first coefficient of quantification is expressed as:

First coefficient of quantification (%)=[(sludge content on calibration curve)/(sludge content as determined by the weight method)]×100.

The same standard samples are colored to varying intensities and measured for the intensity of scattered light and the transmitted light value. Such measurements for the intensity of scattered light and the transmitted light value are conducted on standard samples having different values of the sludge content. The data thus obtained for the intensity of scattered light and the transmitted light value on the colored standard samples in the example under consideration can be related to the sludge content as determined by the weight method and the relationship is shown graphically in FIG. 6.

Figure 8:
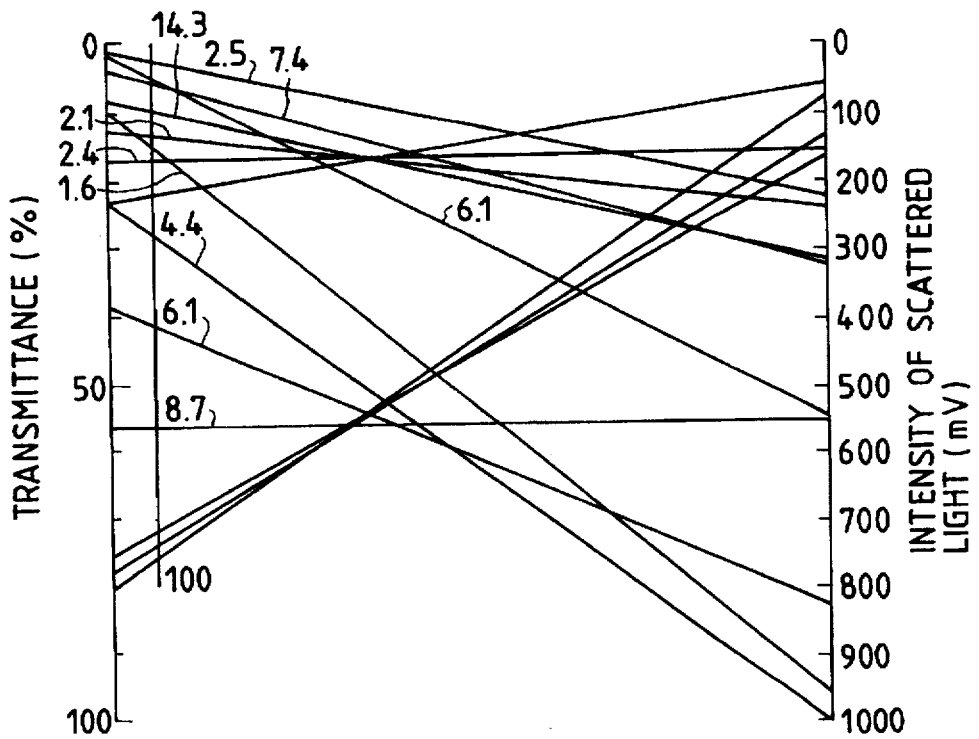
FIG. 8 is a diagram showing how to construct a nomograph representing the relationship between the transmittance, the intensity of scattered light and the coefficient of quantification of scattered light.

The thus established first correlationship, or the relationship between the absorbance (or transmittance), the intensity of scattered light and the first coefficient of quantification, may be represented by nomograph as shown in FIGS. 7 and 8. The axis on the right side of the nomograph in FIGS. 7 and 8 plots the intensity of scattered light on a linear scale whereas the axis on the left side plots the transmitted light value on a linear scale. The axis for the first coefficient of quantification is drawn between the right and left axes such that a series of points at which the line connecting the right axis plotting the intensity of scattered light and the left axis plotting the transmitted light value crosses the axis for the first coefficient of quantification are arranged in the order of the magnitude of the first coefficient of quantification.

Therefore, once the first correlationship which holds between the absorbance or transmittance, the intensity of scattered light and the first coefficient of quantification has been established on the basis of the results of measurement on colored standard samples that differ in color intensity and sludge content, one can determine the first coefficient of quantification for any unknown colored oil sample by measuring its transmitted light value and the intensity of scattered light from it.

Figure 9:
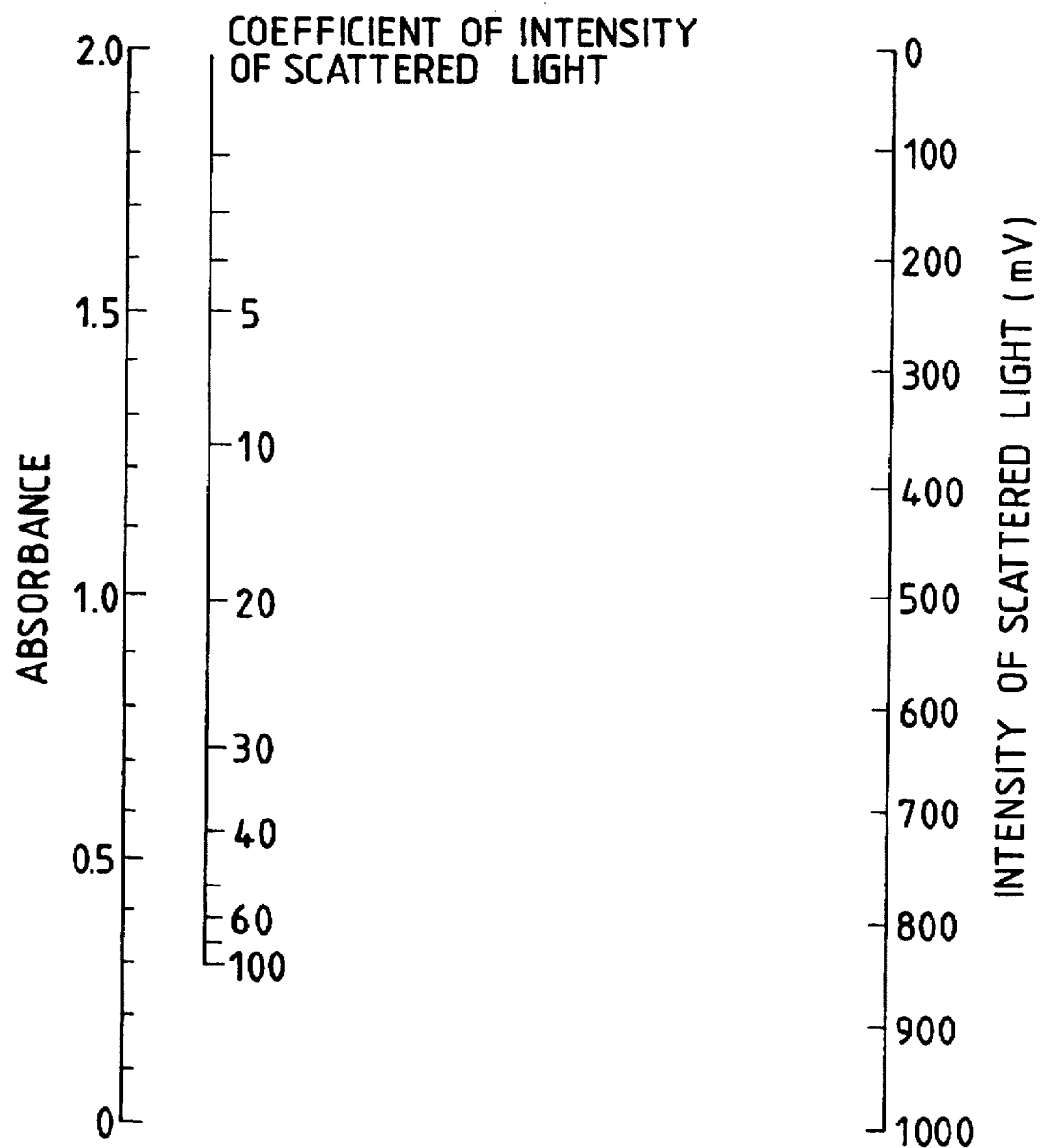
FIG. 9 is a nomograph showing the first correlationship, or the relationship between the absorbance, the intensity of scattered light and the coefficient of quantification of scattered light.
Figure 10:
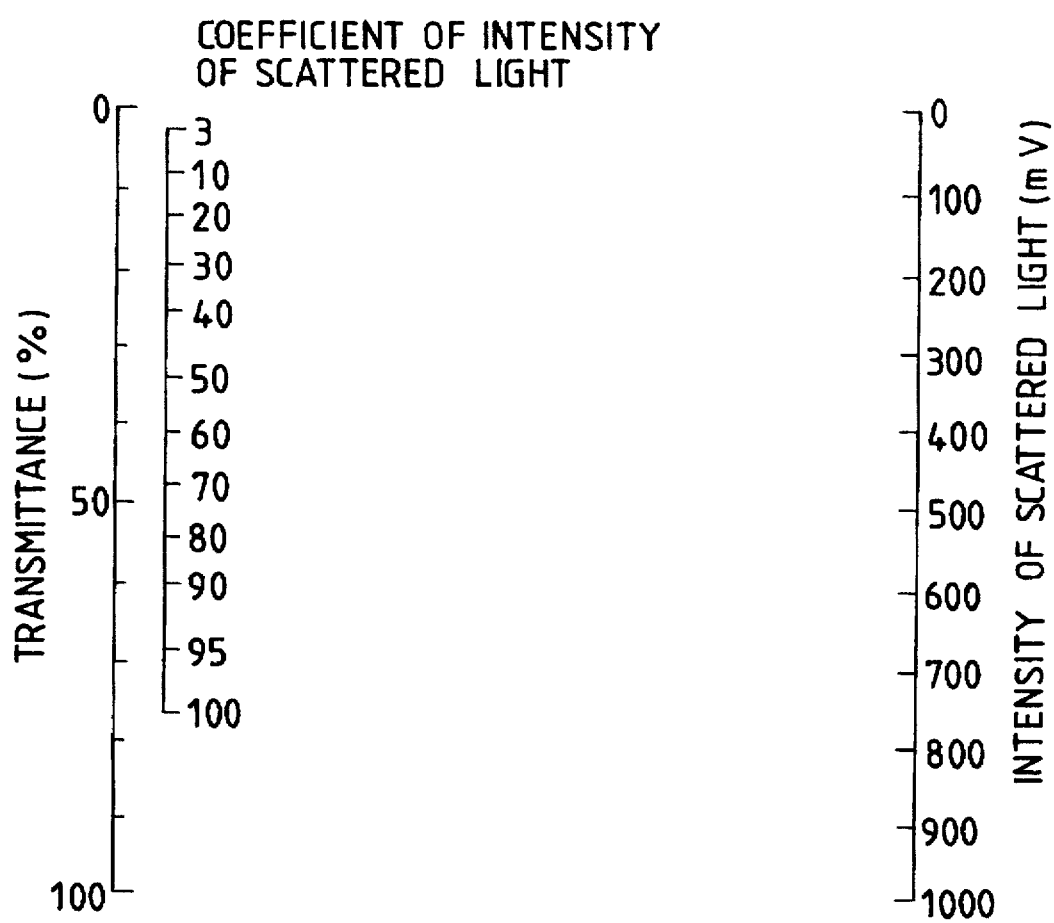
FIG. 10 is a nomograph showing the first correlationship, or the relationship between the transmittance, the intensity of scattered light and the coefficient of quantification of scattered light.

The first correlationship may be represented by a nomograph as shown in FIGS. 9 and 10 or, alternatively, it can be represented by a numerical expression and entered into computer 38. FIGS. 9 and 10 are the same as FIGS. 7 and 8, respectively, except that the axis for the first coefficient of quantification is drawn on a different scale.

The first correlationship can be represented by a numerical expression as follows:

$$P_1 = Pa - Pc \quad (2)$$

where $P_1$: corrected intensity of scattered light (mV)

Pa: voltage (mV) indicative of scattered light from the colored standard sample

Pc: voltage (mV) indicative of scattered light from a standard sample.

(1) The case of determining the first coefficient of quantification (E) from the absorbance and the intensity of scattered light:

$$D \geq 47 \quad E = 1.946D - 56.47 \quad (3a)$$
$$20 \leq D < 47 \quad E = 0.0206D^2 - 0.614D + 18.13 \quad (3b)$$
$$D < 20 \quad E = 1.281D^2 + 0.2261D + 8.793 \quad (3c)$$

where $D: -58.36A + 0.00492P_1 + 85.36$

A: measured absorbance as determined by Eq. (1)

$P_1$: corrected intensity of scattered light (mV) as determined by Eq. (2).

(2) The case of determining the first coefficient of quantification (E) from the transmittance and the intensity of scattered light:

$$E = -0.0000624D^3 + 0.00937D^2 + 0.662D + 2.39 \quad (3d)$$

where $D: 1.365T + 0.015P_1 - 3.59$

T: measured quantity of transmittance as determined by Eq. (1')

$P_1$: corrected intensity of scattered light (mV) as determined by Eq. (2).

How to Establish the Second Correlationship which Determines the Second Coefficient of Quantification for Making Correction for the Size of Sludge Particles There is next described an example of the method of establishing the second correlationship between the relative intensity of scattered light and the second coefficient of quantification.

The method starts with preparing standard samples that contain 0–5.0% of sludge particles in varying sizes. Then, the intensity of scattered light and the transmitted light value are measured with the apparatus 10. The measurement is performed for two cases: one where the apparatus 10 is not equipped with interference filter 40 and the intensity of scattered light over the entire wavelength range, as well as the transmitted light value of either absorbance or transmittance over the entire wavelength range are measured, and the other case is where the apparatus 10 is equipped with interference filter 40 and the intensity of scattered light in the long wavelength range, as well as the transmitted light value of either absorbance or transmittance in the long wavelength range are measured.

Subsequently, the first coefficient of quantification is determined in accordance with the first correlationship on the basis of the intensities of scattered light and the absorbances or transmittances as measured over the entire wavelength range, and the corrected intensities of scattered light are measured over the entire wavelength range by the following equation:

Corrected intensity of scattered light over the entire wavelength range=[(intensity of scattered light over the entire wavelength)/(first coefficient of quantification)] ×100.

Similarly, the corrected intensities of scattered light are measured in the long wavelength range on the basis of the intensities of scattered light and the absorbances or transmittances as measured in the long wavelength range. In the next step, the corrected intensity of scattered light in the long wavelength is subtracted from the corrected intensity of scattered light over the entire wavelength range to measure the corrected intensity of scattered light in the short wavelength range. Then, the relative intensity of scattered light is measured by the following equation:

Relative intensity of scattered light=(Corrected intensity of scattered light in the short wavelength range)/(corrected intensity of scattered light in the long wavelength range)

In the example under consideration, the intensity of scattered light in the short wavelength range is measured from the intensity of scattered light in the long wavelength range and the intensity of scattered light over the entire wavelength range and it is divided by the intensity of scattered light in the long wavelength range to measure the relative intensity of scattered light. Similarly, other expressions of the relative intensity of scattered light can be measured, such as (long wavelength/short wavelength), (short wavelength/entire wavelength), (entire wavelength/short wavelength), (long wavelength/entire wavelength), and (entire wavelength/long wavelength).

On the basis of the relative intensity of scattered light for the standard samples and the sludge content as determined by the weight method, the correlationship between the second coefficient of quantification (to be defined below) and the relative intensity of scattered light (which correlationship is hereunder referred to as "the second correlationship") is established. The second coefficient of quantification is expressed as:

Second Coefficient Of Quantification (%)=[(sludge content as corrected for the intensity of transmitted light)/(sludge content as determined by the weight method)]×100.

Figure 11:
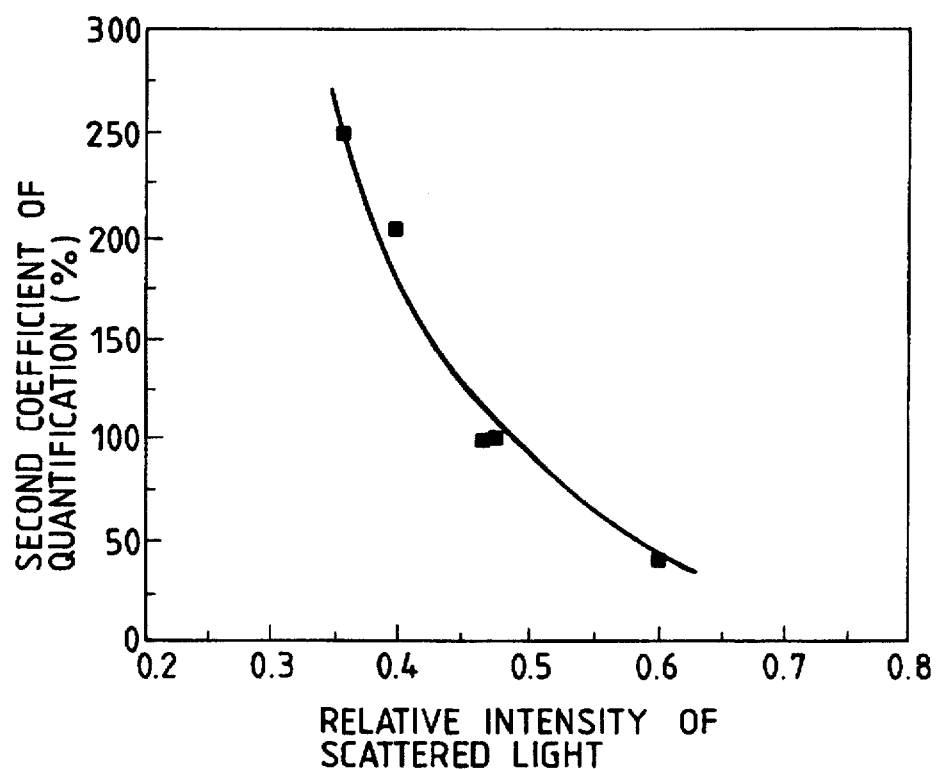
FIG. 11 is a nomograph showing the second correlationship, or the relationship between the second coefficient of quantification and the relative intensity of scattered light.

The second correlationship as obtained in the example under consideration is represented graphically in FIG. 11. If the second correlationship is represented by a numerical expression and entered into computer 38, processing operations can be performed through the following steps.

First, the second correlationship can be represented by a numerical expression as follows:

(1)

$$P_2=Pb-Pd \quad (4)$$

where $P_2$: corrected intensity of scattered light (mV) with filter mounted

Pb: voltage (mV) indicative of scattered light from the colored standard sample with filter mounted Pd: voltage (mV) indicative of scattered light from the standard sample with filter mounted.

(2) On the basis of the intensity of scattered light ($P_1$) and the absorbance (A) or transmittance (T) which have been measured with no filter mounted in the apparatus 10, as well as the intensity of scattered light ($P_2$) and the absorbance ($A_1$) or transmittance (T) which have been measured with filter mounted in the apparatus, the first coefficient of quantification (E) with no filter mounted and the first coefficient of quantification ($E_1$) with filter mounted are determined in accordance with Eq. (3) and the corrected intensity of scattered light over the entire wavelength range ($P_3$) and the intensity of scattered light in the long wavelength range ($P_4$) are measured by the equations that follow.

Absorbance $A_1$ is measured by the equation $A_1=\log((T_3-T_0)/(T_2-T_0))$, and transmittance T is measured by the equation $T=[(T_2-T_0)/(T_3-T_0)]\times 100$.

where $T_3$: voltage (mV) indicative of transmitted light from decane (used as a transparent blank sample) with filter mounted $T_0$: voltage (mV) indicative of transmitted light with the optical path blocked;

$T_2$: voltage (mV) indicative of transmitted light from the standard sample with filter mounted.

$$P_3=P_1/E\times 100 \quad (i)$$

where $P_3$: the corrected intensity of scattered light (mV) with no filter mounted;

$P_1$: the intensity of scattered light (mV) with no filter mounted;

E: the first coefficient of quantification (%) with no filter mounted.

$$P_4=P_2/E_1\times 100 \quad (ii)$$

where $P_4$: the corrected intensity of scattered light (mV) with filter mounted;

$P_2$: the intensity of scattered light (mV) with filter mounted;

$E_1$: the first coefficient of quantification (%) with filter mounted.

(3) The sludge content on calibration curve is determined for an oil sample of interest by the following equation.

$$Ds=P_3\times K$$

where

Ds: sludge content (wt %) on calibration curve;

$P_3$: the corrected intensity of scattered light (mV) with no filter mounted;

K: the content of dry sludge (wt %) per unit intensity of scattered light (mV) and assumes a constant value of $6.29\times 10^{-4}$; if the standard sample is one having a fixed particle size as exemplified by a polystyrene latex and if it includes 1–μm particles, the K value assumes $1.66\times 10^{-4}$ since the voltage indicative of scattered light at a sludge content of 0.2% is 1200 mV (see FIG. 14).

(4) Measure the intensity of scattered light in the short wavelength range by the following equation:

$$P_5=P_3-P_4$$

where $P_5$: the intensity of scattered light (mV) in the short wavelength range with no filter mounted;

$P_3$: the corrected intensity of scattered light (mV) with no filter mounted;

$P_4$: the corrected intensity of scattered light (mV) with filter mounted.

(5) Measure the relative intensity of scattered light by the following equation:

$$P_r=P_5/P_4$$

where $P_p$: the relative intensity of scattered light;

$P_S$: the intensity of scattered light (mV) in the short wavelength range with no filter mounted;

$P_4$: the corrected intensity of scattered light (mV) with filter mounted. (6) Determine the second coefficient of quantification X by the following equation:

$$X = 3542 P_p^2 - 4306 P_p + 1347$$

where

X: the second coefficient of quantification;

$P_p$: the relative intensity of scattered light.

Method of Determination Using a Nomograph

The procedure of determination using a homograph is described below.

(1) Measure the intensities of scattered and transmitted light components from an oil sample of interest by the apparatus 10. To this end, the following steps are taken.

i) Measure about 0.5 g of the oil sample in a Petri dish; heat in a dryer (air bath) at 100° C. for 30 min to remove water from the oil sample;

ii) Place about 0.05 g of the oil sample in the 0.1–mm cell and close it with the cover tightly. Since the optical axis of the turbidimeter has a diameter of 6 mm, the amount of the oil sample in the cell is sufficient to fill the area of the optical axis;

iii) Insert the cell into the first slot in the cell holder, heat at 70° C., and read off the voltages indicative of transmitted and scattered light components both before and after an interference filter is mounted in the apparatus;

iv) Block the optical path and read off the voltage indicative of transmitted light both before and after the interference filter is mounted;

v) Insert a decane containing cell into the optical path and read off the voltage indicative of transmitted light both before and after the interference filter is mounted; and vi) Insert a colored standard sample into the optical path and read off the voltage indicative of the intensity of scattered light both before and after the interference filter is mounted.

(2) Determine the sludge content on calibration curve from the measured intensity of scattered light in accordance with the calibration curve in FIG. 5.

(3) Calculate the transmitted light value of either absorbance or transmittance from the measured intensity of transmitted light.

(4) Determine the first coefficient of quantification in accordance with FIGS. 9 and 10 on the basis of the calculated absorbance (or transmittance) and the measured intensity of scattered light.

(5) The sludge content as corrected for the intensity of transmitted light is determined by the following equation on the basis of the sludge content on calibration curve and the first coefficient of quantification:

Sludge content corrected for the intensity of scattered light=[(sludge content on calibration curve)/(first coefficient of quantification)]×100.

(6) Measure the relative intensity of scattered light and determine the second coefficient of quantification from FIG. 11.

(7) The sludge content as corrected for both the intensity of transmitted light and the particle size is determined by the following equation on the basis of both the sludge content as corrected for the intensity of transmitted light and the second coefficient of quantification:

Sludge content corrected for both the intensity of transmitted light and the particle size=[(sludge content corrected for the intensity of transmitted light)/(second coefficient of quantification)]×100.

Method of Determination Using Expressions

There is now described the method of determination using expressions.

(1) As is the method of determination using a nomograph, oil samples are prepared and subjected to determinations; then, the first coefficient of quantification $E_1$ and the second coefficient of quantification X are determined from the measured values in accordance with the associated equations set forth above.

(2) Determine the sludge content as corrected for the intensity of transmitted light and use the following equation to determine the sludge content as corrected for both the intensity of transmitted light and the particle size:

$$DS = (Ds/X) \times 100$$

where

DS: the sludge content corrected for both the intensity of transmitted light and the particle size;

Ds: the sludge content corrected for the intensity of transmitted light;

X: the second coefficient of quantification.

Determination Test (Calculating the Sludge Content by Expressions)

The sludge content of oil sample No. 1 was determined using expressions.

(1) The sludge content a per unit intensity of scattered light (mV) was predetermined to be $6.29 \times 10^{-4}$ (%).

(2) Results of determinations (mV) on various substances.

| | | |
|---|---|---|
| b: | voltage indicative of transmitted light with the optical path shut off | 5180 |
| c: | voltage indicative of transmitted light from decane before mounting an interference filter | 8943 |
| d: | voltage indicative of transmitted light from decane after mounting the interference filter | 7965 |
| e: | voltage indicative of scattered light from a colored standard before mounting the interference filter | 5175 |
| f: | voltage indicative of scattered light from the colored standard after mounting the interference filter | 5175 |
| g: | voltage indicative of transmitted light from a sample of interest before mounting the interference filter | 5700 |
| h: | voltage indicative of scattered light from the sample of interest before mounting the interference filter | 4268 |
| i: | voltage indicative of transmitted light from the sample of interest after mounting the interference filter | 5628 |
| j: | voltage indicative of scattered light from the sample of interest after mounting the interference filter | 4433 |

(3) Processing operations (i) Using absorbance:

The absorbance of the sample before mounting the interference filter:

$$k = \log((c-b)/(g-b)) = 0.859$$

The absorbance of the sample after mounting the interference filter:

$m = \log((d-b)/(i-b)) = 0.793$

The intensity of scattered light from the sample before mounting the interference filter:

$n = e-h = 907$

The intensity of scattered light from the sample after mounting the interference filter:

$o = f-j = 742$

The coefficient of quantification of scattered light (q) before mounting the interference filter:

$p = -58.36k + 0.00492n + 85.26 = 39.59$ $q = 0.0206P^2 - 0.614p + 18.13 = 26.11$

The coefficient of quantification of scattered light(s) after mounting the interference filter:

$r = -58.36m + 0.00492o + 85.26 = 42.63$ $s = 0.0206r^2 - 0.614r + 18.13 = 29.39$

The corrected intensity of scattered light before mounting the interference filter:

$t = n/q \times 100 = 3474$

The corrected intensity of scattered light after mounting the interference filter:

$u = o/s \times 100 = 2524$

The sludge content of the sample as corrected for the intensity of transmitted light:

$v = t \times a = 2.19$

The intensity of scattered light in the short wavelength range:

$w = t-u = 950$

The relative intensity of scattered light:

$x = w/u = 0.376$

The second coefficient of quantification:

$y = 3542x^2 - 4306x + 1347 = 228.7$

The sludge content as corrected for both the intensity of transmitted light and the particle size:

$z = v/y \times 100 = 0.96$ (ii) Using Transmittance:

In the case of using transmittance, the symbols k, m, p, q, r and s defined above are replaced by the following k', m', p', q', r' and s', respectively.

The transmittance of the sample before mounting the interference filter:

$k' = [(g-b)/(c-b)] \times 100 = 13.8$

The transmittance of the sample after mounting the interference filter:

$m' = [(i-b)/(d-b)] \times 100 = 16.1$

The coefficient of quantification of scattered light (q') before mounting the interference filter:

$p' = 1.356k' + 0.015n - 3.59 = 28.9$ $$\begin{aligned} q' &= -0.0000624p'^3 + 0.00937p'^2 + 0.663p' + 2.39 \\ &= 27.8 \end{aligned}$$

The coefficient of quantification of scattered light (s') after mounting the interference filter:

$r' = 1.36m' + 0.015n - 3.59 = 32.0$ $$\begin{aligned} s' &= -0.000064r'^3 + 0.00937r'^2 + 0.662r' + 2.39 \\ &= 31.1 \end{aligned}$$

Subsequently, the sludge content corrected for both the intensity of transmitted light and the particle size can be determined using q' and s' as in (i).

It took only about 10 min. to determine the sludge content of oil sample No. 1.

Similarly, oil sample Nos. 2–6 were determined for their sludge content and the results are shown in Table 2 in comparison with the data obtained by applying the weight method to the same oil samples. Again, it took only about 10 min. to complete the determination on each sample in accordance with the method of the present invention.

As one can see from Table 2, the values of sludge content determined by the method of the present invention were very close to the data obtained by the weight method and, what is more, the required time of determinations was extremely short compared to the weight-method.

TABLE 2

| Sample No. | Sludge content (wt %) | |
| --- | --- | --- |
| | Inventive method | Weight method |
| 1 | 0.96 | 1.0 |
| 2 | 0.01 | 0.03 |
| 3 | 0.04 | 0.05 |
| 4 | 0.33 | 0.31 |
| 5 | ≦0.01 | 0.02 |
| 6 | 1.62 | 1.72 |

Note:
Sample Nos. 1, 2, 4 and 5 were bunker residual fuel oil and sample Nos. 3 and 6 were hydrocracked oil.

Figure 12:
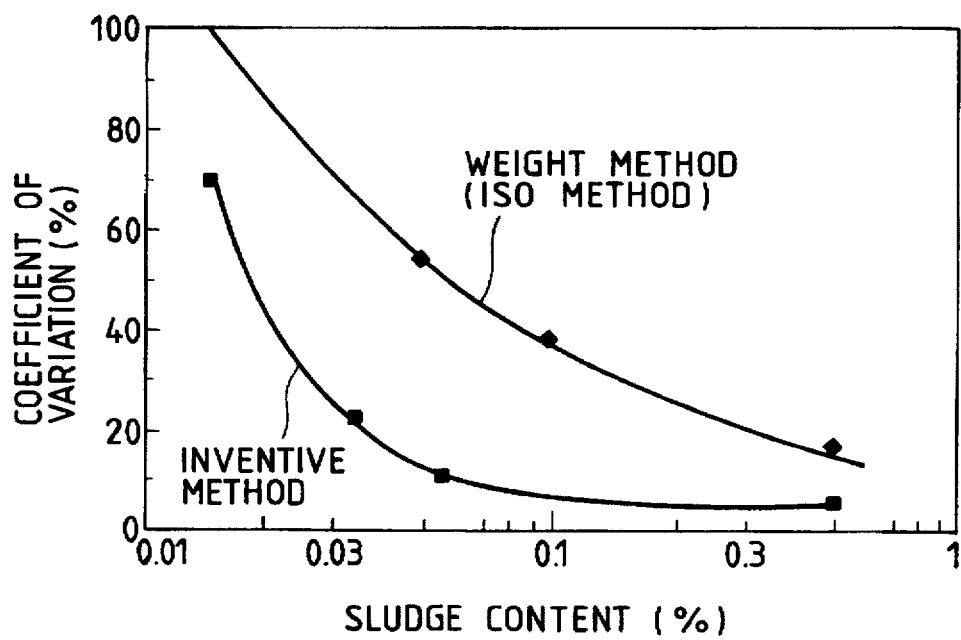
FIG. 12 is a graph showing the coefficient of variation vs the sludge content for the weight method and the method of the present invention.

The coefficient of variation of the values of determination by the method of present invention is shown in FIG. 12 as a function of the sludge content in comparison with the coefficient of variation of the data obtained by the weight method. As one can see from FIG. 12, the values of determination by the method of the present invention have a smaller coefficient of variation than the data obtained by the weight method in a low-sludge region and, hence, the method of the present invention has a higher precision of determination than the weight method, particularly in the region where the sludge content is 1.0% or less.

While the method of the present invention has been described above with particular reference made to the case of performing processing operations using expressions, it should be noted that the sludge content can be determined on the same oil samples using a nomograph, as illustrated just below.

Determination Test (Calculating the Sludge Content with the Aid of a Nomograph)

As an alternative method to the calculation by expressions, a nomographic technique was used to determine the sludge content of oil sample No. 1. The procedure of this technique and the results are described below.

(1) On the basis of the results of determinations on various substances as performed by the aforementioned technique of calculating the sludge content by expressions [see, in particular, the description under (2)], similar processing operations were conducted as follows.

The absorbance of the sample before mounting the interference filter:

$k = \log((c-b)/(g-b)) = 0.859$

The absorbance of the sample after mounting the interference filter:

$m = \log((d-b)/(i-b)) = 0.793$

The intensity of scattered light from the sample before mounting the interference filter:

$n = e-h = 907$

The intensity of scattered light from the sample after mounting the interference filter:

$o = f-j = 742.$

When using transmittance in place of absorbance, symbols k and m are replaced by k' and m', respectively, as defined below:

k'=[(g−b)/(c−b)]×100=13.8 m'=[(i−b)/(d−b)]×100=16.1

(2) Subsequently, the coefficient of quantification of scattered light (q) before mounting the interference filter was determined from a nomograph.

To this end, the nomograph represented on FIG. 9 was used and a line was drawn to connect 0.859 on the left axis of the nomograph (i.e., the absorbance of the oil sample before mounting the interference filter) and 907 on the right axis (i.e., the intensity of scattered light from the oil sample); then, the coefficient of quantification of scattered light (q) was read off as 26 at the point where the line crossed the center axis plotting the coefficient of quantification of scattered light.

(If transmittance is to be used in place of absorbance, similar procedures are taken such that the coefficient of quantification of scattered light (q') from the oil sample before mounting the interference filter is measured from the nomograph represented on FIG. 10.

To this end, a line was drawn to connect 13.8 on the left axis of the nomograph (i.e., the transmittance of the oil sample before mounting the interference filter) and 907 on the right axis (i.e., the intensity of scatter light from the oil sample); then, the coefficient of quantification of scattered light (q') was read off as 28 at the point where the line crossed the center axis plotting the coefficient of quantification of scattered light.)

(3) Subsequently, the coefficient of quantification of scattered light (s) after mounting the interference filter was measured from a nomograph.

To this end, the nomograph represented on FIG. 9 was again used and a line was drawn to connect 0.793 on the left axis of the nomograph (i.e., the absorbance of the oil sample after mounting the interference filter) and 742 on the right axis (i.e., the intensity of scattered light from the oil sample); then, the coefficient of quantification of scattered light (s) was read off as 29 at the point where the line crossed the center axis plotting the coefficient of quantification of scattered light.

(If transmittance is to be used in place of absorbance, similar procedures are taken such that the coefficient of quantification of scattered light (s') after mounting the interference filter is measured from the nomograph represented on FIG. 10.

To this end, a line was drawn to connect 16.1 on the left axis of the nomograph (i.e., the transmittance of the oil sample after mounting the interference filter) and 742 on the right axis (i.e., the intensity of scattered light from the oil sample); then, the coefficient of quantification of scattered light (s') was read off as 31 at the point where the line crossed the center axis plotting the coefficient of quantification of scattered light.)

(4) In the next step, processing operations were performed in the following manner (if transmittance is to be substituted for absorbance, q and s shall be replaced by q' and s', respectively, in the following operations).

The corrected intensity of scattered light before mounting the interference filter was measured:

t=n/q×100=3488

The corrected intensity of scattered light after mounting the interference filter was measured:

u=o/s×100=2559

The uncorrected dry sludge content of the sample was determined:

v=t×a=2.19

The intensity of scatted light in the short wavelength range was measured:

w=t−u=960

The relative intensity of scattered light by wavelength range was measured:

x=w/u=0.375

(5) The second coefficient of quantification was determined from the graph in FIG. 11:

y=230

(6) Finally, the sludge content as corrected for both the intensity of transmitted light and the particle size was determined by the following equation:

z=v/y×100=0.95

Application of the Inventive Method to Testing the Thermal Stability of Residual Fuel Oils As an example of the use of the method according to the present invention, its application to testing the thermal stability of residual fuel oils is described below. First, two types of residual fuel oil, A and N, both based on a hydrocracked oil were provided and the sludge content of each sample was determined by the method of the present invention. Then, the two samples were held in an oil bath at 100° C. for about 24 h and, thereafter, the sludge content of each sample was again determined by the method according to the present invention. Subsequently, the thermal change in sludge content was calculated on each sample to evaluated the stability of residual fuel oils A and B.

The results of determination of the sludge content of each sample by the method according to the present invention are shown in Table 3 in comparison with the data obtained by the weight method. Obviously, the results of determinations by the method according to the present invention are very close to the data obtained by the weight method. It is therefore concluded that the method of the present invention can be used to evaluate the stability of residual fuel oils.

TABLE 3

| | | Sludge content (wt %) | |
|---|---|---|---|
| | | Inventive method | Weight method |
| Sample A | 0 h | 0.02 | ≦0.05 |
| | 24 h | 0.40 | 0.42 |
| Sample B | 0 h | 0.05 | 0.07 |
| | 24 h | 0.47 | 0.46 |

Application of the Inventive Method to the Determination of the Amine-Pentane Insolubles in Lubricants The amine-pentane insoluble content of lubricants is conventionally determined in accordance with ASTM D893 (the centrifugal weight method). This method includes diluting an oil of interest (10 g) with pentane containing a flocculant (amine) to prepare a sample (100 ml), repeating the steps of washing with pentane and centrifugation, drying the sediment and weighing it to determine the mass of the amine-pentane insoluble content. Thus, the method under ASTM D893 must be implemented with a bulky apparatus that not only uses a centrifuge but also requires a prolonged period of time to complete the determination.

Under the circumstances, the present inventor reviewed the applicability of the inventive method to the determination of the amine-pentane insolubles in lubricants. The study started with constructing a calibration curve representing the relationship between the intensity of scattered light and the values of the amine-pentane insoluble content as determined by the ASTM method. Then, an oil sample yet to be diluted with a solvent was put into a sample cell having a groove 0.02 mm deep and the necessary parameters such as absorbance and the intensity of scattered light were measured. Thereafter, the first coefficient of quantification for making correction for the intensity of transmitted light and the second coefficient of quantification for making correction for the particle size are determined in accordance with the procedures specified by the invention and these two coefficients are used to correct the amine-pentane insoluble content of the oil sample that has been determined on the calibration curve.

The results of determinations by the method of the invention are shown in Table 4 in comparison with the data obtained by the ASTM method. As one can see from Table 4, the inventive method is applicable to the determination of the amine-pentane insoluble content in lubricants.

TABLE 4

| | | Amine-pentane insoluble content (wt %) | |
|---|---|---|---|
| | | Inventive method | ASTM method |
| 1. | Oil used on diesel engine | 0.62 | 0.64 |
| 2. | do. | 1.1 | 1.2 |
| 3. | do. | 1.7 | 1.6 |
| 4. | do. | 2.1 | 2.1 |

Application of the Inventive Method to the Analysis of Asphaltene in Residual Fuel Oils The content of asphaltene in residual fuel oils is conventionally determined in accordance with IP-143/90, UOP 614-68 and ASTM D3279-90. The "asphaltene" is commonly defined as components that are soluble in toluene but insoluble in heptane. Therefore, the methods identified above are basically techniques that depend on fractionation by solvents and, involving filtration and extraction steps, they require cumbersome operations and a prolonged time for analysis.

The content of asphaltene in residual fuel oils could be determined rapidly by the method described in U.S. Pat. No. 4,843,247. According to this method, a sample to be determined is dissolved in an aromatic solvent and warm n-heptane is added to prepare a sample suspension in which asphaltene is suspended as particles of uniform size. Then, the absorbance of the sample suspension is measured at two wavelengths and the two obtained values of absorbance are calculated for division to the absorbance of asphaltene and the absorbance of the n-heptane soluble content. The asphaltene content can be determined from the absorbance of asphaltene. The problem with this technique is that if the asphaltene content is low enough to increase the absorbance of the n-heptane soluble content, the precision of analysis by the technique is poor; therefore, the method of U.S. Pat. No. 4,843,247 is not applicable to samples having low asphaltene contents.

Under the circumstances, the present inventor reviewed the applicability of the inventive method to the determination of the asphaltene content in residual fuel oils. The study started with preparing sample suspensions in accordance with U.S. Pat. No. 4,843,247 using as a standard the asphaltene content obtained by the UOP method. Then, a calibration curve was constructed that represented the relationship between the intensity of scattered light and the values of the asphaltene content as determined by the UOP method. In the next step, each sample suspension was put into a sample cell of 2 mm in size and the necessary parameters such as absorbance (or transmittance) and the intensity of scattered light were measured. Subsequently, in accordance with the procedures specified by the invention, the intensity of scattered light was corrected and the first coefficient of quantification for making correction for the intensity of transmitted light, as well as the second coefficient of quantification for making correction for the particle size were determined with the aid of nomographs or expressions; these two coefficients were used to correct the asphaltene content of each sample suspension that has been determined on the calibration curve.

The results of determinations by the method of the invention are shown in Table 5 in comparison with the data obtained by the UOP method. As one can see from Table 5, the inventive method achieved satisfactory precision with a sample containing less than 0.1 wt % asphaltene and, hence, it is applicable to the determination of the asphaltene content in residual fuel oils.

TABLE 5

| | Asphaltene content (wt %) | |
|---|---|---|
| Sample No. | Inventive method | UOP method |
| 1 | 15.3 | 15.8 |
| 2 | 4.59 | 4.43 |
| 3 | 3.36 | 3.31 |
| 4 | 0.84 | 0.80 |
| 5 | 0.37 | 0.34 |
| 6 | 0.021 | 0.025 |

What is claimed is:

1. A method of determining contents of insolubles in oils, which comprises the steps of:

(a) constructing a calibration curve from an intensity of scattered light which is obtained by emitting light into a standard oil;

(b) establishing a first correlationship for correcting a first determination error in a content of insolubles that is caused by a color intensity of a subject oil and a relative proportion of the insolubles;

(c) establishing a second correlationship for correcting a second determination error in the content of the insolubles that is caused by a difference in particle size of the insolubles;

(d) measuring an intensity of scattered light and a transmitted light value for the subject oil, and obtaining from the calibration curve a content level of insolubles corresponding to the measured scattered light and obtaining a first corrected content by correcting the content level using the first correlationship established in the step (b); and (e) obtaining a second corrected content of the insolubles by correcting the first corrected content obtained in the step (d) using the second correlationship established in the step (c).

2. A method of claim 1, wherein in the step (b), the first correlationship comprises a first coefficient of quantification which is determined by an intensity of scattered light and a transmitted light value which are measured for the standard oil, the first coefficient being obtained by determining a relationship of a content of insolubles determined by the calibration curve constructed in the step (a) to a content of insolubles determined by directly applying the standard oil to a filter, the transmitted light value comprising an absorbance or a transmittance for the standard oil, wherein in the step (c), the second correlationship comprises a second coefficient of quantification which is determined by a relative intensity of scattered light calculated from first and second intensities of scattered light for a first light and a second light of the light emitted into the standard oil in accordance with the first correlationship, the first light and the second light being selected from the group consisting of a first light component having an entire wavelength range of emitted light, a second light component having wavelengths longer than a predetermined value in the entire wavelength range, and a third light component having wavelengths shorter than the predetermined value in the entire wavelength range.

3. A method of claim 2, wherein the standard oil includes the insolubles having a fixed particle size and a fixed content which are previously determined.

4. A method of claim 2, wherein the predetermined value comprises a wavelength within a range from 200 to 950 nm.

5. A method of claim 2, wherein the first coefficient of quantification is obtained through either a predetermined nomograph or predetermined expressions which represent a relationship between the intensity of scattered light and the transmitted light value which are measured for the standard oil in accordance with the content of insolubles determined by directly measuring the standard oil.

6. A method of claim 2, wherein the relative intensity of scattered light comprises a ratio selected from the group consisting of a ratio of the intensity of scattered light for the second light component to that of scattered light for the third light component, a ratio of the intensity of scattered light for the third light component to that of scattered light for the first light component, a ratio of the intensity of scattered light for the first light component to that of scattered light for the third light component, a ratio of the intensity of scattered light for the second light component to that of scattered light for the first light component, and a ratio of the intensity of scattered light for the first light component to that of scattered light for the second light component.

7. An apparatus for determining contents of insolubles in oils, which comprises:

a cell holding oil which is to be examined;

an optical system emitting light having a predetermined light component into the cell;

a light-receiving device comprising a first sensor measuring an intensity of scattered light and a second sensor measuring an intensity of transmitted light passing through the cell to output electric signals; and a calculating device connected to the light-receiving device for determining a content of insolubles in the oil in accordance with the electric signals, the calculating device correcting a first determination error in a content of insolubles that is caused by a color intensity of the oil and a relative proportion of the insolubles, and correcting a second determination error that is caused by a difference in particle size of the insolubles.

8. An apparatus of claim 7, wherein the calculating device stores:

a calibration coefficient for obtaining the content of the insolubles from the intensity of scattered light which is measured by the light-receiving device;

a first coefficient of quantification for correcting the first determination error in accordance with the intensity of scattered light and a transmitted light value calculated from the intensity of transmitted light which are measured by the light-receiving device, wherein the first coefficient of quantification is obtained by determining a relationship of the content of the insolubles determined by the calibration coefficient to a content of insolubles determined by directly applying the oil to a filter, the transmitted light value comprising an absorbance or a transmittance for the oil; and a second coefficient of quantification for correcting the second determination error in accordance with a relative intensity of scattered light calculated from the first coefficient and first and second intensities of scattered light for a first light and a second light emitted by the optical system, wherein the second coefficient of quantification is obtained by determining a relationship of the content of the insolubles determined by the calibration coefficient to a content of insolubles determined by directly applying the oil to a filter through the relative intensity of scattered light, wherein the first light and the second light are selected from the group consisting of a first light component having an entire Wavelength range of emitted light, a second light component having wavelengths longer than a predetermined value in the entire wavelength range, and a third light component having wavelengths shorter than the predetermined value in the entire wavelength range.

9. An apparatus of claim 7, wherein the oil includes the insolubles having a fixed particle size and a fixed content which are previously determined.

10. An apparatus of claim 7, wherein the predetermined value comprises a wavelength within a range from 200 to 950 nm.

11. An apparatus of claim 7, wherein the first coefficient of quantification is obtained through either a predetermined nomograph or predetermined expressions which represent a relationship between the intensity of scattered light and the transmitted light value in accordance with the content of insolubles determined by directly applying the oil to the filter.

12. An apparatus of claim 7, wherein the relative intensity of scattered light comprises a ratio selected from the group consisting of a ratio of the intensity of scattered light for the second light component to that of scattered light for the third light component, a ratio of the intensity of scattered light for the third light component to that of scattered light for the first light component, a ratio of the intensity of scattered light for the first light component to that of scattered light for the third light component, a ratio of the intensity of scattered light for the second light component to that of scattered light for the first light component, and a ratio of the intensity of scattered light for the first light component to that of scattered light for the second light component.

* * * * *